United States Patent
Guirguis et al.

(10) Patent No.: US 6,296,764 B1
(45) Date of Patent: Oct. 2, 2001

(54) APPARATUS FOR MIXING AND SEPARATING PARTICULATE MATTER FROM A FLUID

(75) Inventors: Raouf A. Guirguis, Vienna, VA (US); Mark T. MacLean-Blevins, Westminster, MD (US)

(73) Assignee: LaMina, Inc., Herndon, VA (US)

( * ) Notice: Subject to any disclaimer, the term of this patent is extended or adjusted under 35 U.S.C. 154(b) by 0 days.

(21) Appl. No.: 09/185,606

(22) Filed: Nov. 4, 1998

Related U.S. Application Data
(60) Provisional application No. 60/064,271, filed on Nov. 4, 1997.

(51) Int. Cl.$^7$ .............................. B01D 33/00; B01F 7/18; B01F 7/24; B01L 3/00
(52) U.S. Cl. ................ 210/323.1; 210/324; 210/319; 210/329; 210/330; 422/101; 422/102; 366/213; 366/214; 366/218; 366/242
(58) Field of Search ................ 210/767, 257.1, 210/257.2, 330, 323.1, 329, 324, 319; 128/760; 422/63, 64, 65, 68.1, 99–102, 103, 104; 436/173, 177; 366/213–214, 218, 242

(56) References Cited

U.S. PATENT DOCUMENTS

| | | | |
|---|---|---|---|
| 3,583,230 | * | 6/1971 | Patterson . |
| 4,479,720 | * | 10/1984 | Mochida et al. ............... 366/214 |
| 4,871,683 | * | 10/1989 | Harris et al. . |
| 4,921,618 | * | 5/1990 | Hamlin ............................ 210/780 |
| 4,953,561 | | 9/1990 | Guirguis ........................ 128/771 |
| 5,016,644 | | 5/1991 | Guirguis ........................ 128/771 |
| 5,042,502 | | 8/1991 | Guirguis ........................ 128/771 |
| 5,137,031 | | 8/1992 | Guirguis ........................ 128/771 |
| 5,139,031 | | 8/1992 | Giurguis ........................ 128/771 |
| 5,143,627 | | 9/1992 | Lapidus et al. ................ 210/767 |
| 5,224,489 | | 7/1993 | Guirguis ........................ 128/771 |
| 5,236,263 | * | 8/1993 | Friedland ....................... 366/213 |
| 5,282,978 | * | 2/1994 | Polk, Jr. et al. ............... 210/767 |
| 5,301,685 | | 4/1994 | Guirguis ........................ 128/760 |
| 5,471,994 | | 12/1995 | Guirguis ........................ 128/760 |
| 5,589,649 | * | 12/1996 | Brinker et al. . |
| 5,624,554 | * | 4/1997 | Faulkner et al. .............. 210/232 |
| 5,816,701 | * | 10/1998 | Martin et al. .................. 366/208 |

* cited by examiner

Primary Examiner—W. L. Walker
Assistant Examiner—Marianne Ocampo
(74) Attorney, Agent, or Firm—Foley & Lardner

(57) ABSTRACT

An apparatus for simultaneously processing a plural number of samples, each of the samples including a fluid containing particulate matter. The apparatus is useful in cytology to collect a uniform monolayer of cells from a biological fluid. Each of a plural number of processing assemblies (corresponding to the plural number of samples) comprises a container, an agitator rotatable relative to the container for contacting and dispersing particulate matter in the fluid, a filter assembly including a filter for collecting particulate matter, and a pump for moving the fluid through the filter. Each container is supported on a separate container receiver, and each pump is engaged by a separate pump engagement. A rotary driver effects relative rotation of the agitators and their respective containers simultaneously to mix the samples in the containers.

20 Claims, 14 Drawing Sheets

APPARATUS FOR MIXING AND SEPARATING PARTICULATE MATTER FROM A FLUID

CROSS-REFERENCE TO RELATED APPLICATIONS

The present invention claims the benefit of priority based on U.S. Provisional Application Ser. No. 60/064,271, filed Nov. 4, 1997.

TECHNICAL FIELD OF THE INVENTION

The present invention is directed to an apparatus and method for collecting a uniform monolayer of particulate matter. In particular, the present invention is directed to an apparatus and manual or semi-automatic method for collecting a uniform monolayer of cells from biological fluids and preparing the monolayer of cells for use in cytological protocols.

BACKGROUND OF THE INVENTION

In a wide variety of technologies, the ability and/or facility for separating matter, typically particulate matter, from a fluid is a critical component in the ability to test for the presence of substances in the fluid. Too often, interference associated with sample preparation obscures the target cells to such a degree that the process is not sufficiently reliable, or too costly.

Such a scenario applies to many other fields which involve detection and/or diagnosis, including environmental testing, radiation research, cancer screening, cytological examination, microbiological testing, and hazardous waste contamination, to name just a few.

In all of these endeavors, limiting factors in the sample preparation protocol include adequately separating particulate matter from its fluid carrier (e.g., physiological fluid, biological fluid and environmental fluid), and easily and efficiently collecting and concentrating the particulate matter in a form readily accessible for microscopic examination.

In the case of cytological examination, a sample of cells is obtained from a patient. Typically, this is done by scraping or swabbing an area, as in the case of cervical samples, or by collecting body fluids, such as those obtained from the chest cavity, bladder, or spinal canal, or by fine needle aspiration. In a conventional manual cytological examination, particulate matter including cells and debris in the fluid are transferred onto a glass slide by smearing and subsequently air-dried. Smearing results in non-uniform densities and uneven distributions of cells and debris that often obscure the target cells. Air drying causes cell distortion and further impedes accurate examination.

It has been found that prompt processing of urine to obtain fresh ensures the accuracy of quantitative culture results, urinalysis and microscopy. Fresh cells tend to stick to a glass slide much better than cells from preserved urine, allowing for smoother cell spread onto the glass body. Delays in processing, negligent care in either inpatient or outpatient settings and lack of refrigeration may lead to non-optimal slide preparation. One known solution to the delay problem is the use of chemical preservatives with the urine. The presence of liquid preservatives, however, in the urine specimen raises the specific gravity of the specimen to unmeasurable levels and may limit the potential usefulness of the urine for various types of traditional quantitative analysis, such as slide microscopy.

Diagnostic microbiology and/or cytology, particularly in the area of clinical pathology, bases diagnoses on a microscopic examination of cells and other microscopic analyses. The accuracy of the diagnosis and the preparation of optimally interpretable specimens typically depends upon adequate sample preparation. New methodologies such as immunocytochemistry and image analysis require preparations that are reproducible, fast, biohazard-free and inexpensive. Conventional cell preparation techniques fail to adequately address the issues of non-uniform cell densities, uneven cell distribution and air drying artifacts.

Conventionally, body fluid samples are collected for cytological examinations using containers that contain a preservative solution for preserving the cytology specimen during shipment from the collection site to the cytology laboratory. Furthermore, cytology specimens collected from the body cavities using a swab, smear, flush or brush are also preserved in containers with fixatives (e.g., alcohol or acetone fixatives) prior to transferring cells onto the slide or membrane for staining or examination.

It is desirable to provide a urine or other biological fluid specimen container that would allow liquid biological specimens to be tested without removing the lid of the urine or biological fluid container. However, none of the prior art solves the problems of transferring cells in a monolayer to a slide for examination without submerging portions of the device in the sample (and increasing the risk of contamination), consistently and repeatedly forming a high quality monolayer on the microscope slide, and processing the sample so that the fluid from which the cells were taken is preserved.

A number of methods, apparatuses, and structures for dispersing cells in the fluid are known. For example, U.S. Pat. No. 5,143,627 opens the sample container, inserts a dispersing element into the liquid suspension, and rotates the dispersing element for several minutes. In another example, the so-called "Saccomanno method" is used to process sputum, a process that is time consuming and involves a large number of processing steps.

In contrast to the conventional techniques, the solid matter preparation techniques of the present invention address the issues of non-uniform matter densities, uneven matter distribution, and sample loss and contamination due to the number of steps involved in the sample preparation. Thus, preparations according to the present invention result in an even distribution of solids that have superior morphology, improved visualization, and are readily positioned and available for light absorbance analysis without the need to further manipulate or prepare the sample.

SUMMARY OF THE INVENTION

The present invention relates to an apparatus and method for collecting matter for detection, analysis, quantification, and/or visualization. The devices and methods of the present invention are particularly suitable for separating particulate matter from biological, physiological, and environmental fluids and presenting the particulate matter in an improved manner for cytological examination.

A preferred embodiment of the present invention relates to an apparatus and method for collecting a uniform layer of cells from urine or other biological fluid specimen in a cytology collection apparatus or assay module, and for transferring the uniform layer of particulate matter to a slide.

The devices and methods of the present invention may be configured into a hand-held manual system or structure, or a partially automated system or structure.

Such an apparatus according to the present invention overcomes the problems associated with conventional equipment for collecting cells and other particles for cytology by providing a mechanism of relatively simple structure and operation that separates particles from a liquid solution, collects an approximately known quantity of the cells in a monolayer, and transfers the collected cells to a microscope slide. In some embodiments of the present invention, no element of the apparatus is placed in the liquid sample, thus preventing unnecessary contamination of the sample. Moreover, in some embodiments of the present invention, the container holding the sample is not opened in the course of collecting and transferring the cells, thus eliminating the possibility of sample contamination during testing.

In all embodiments of the present invention, a monolayer of the particulate matter, e.g., cells, in the sample is collected on a filter by passing two branches of a fluid flow through and around the filter. Such a filter is known from U.S. Pat. Nos. 5,301,685 and 5,471,994, which are incorporated by reference.

The patient or medical person handling the collection may seal a separate container. The collection of the cells according to the present invention allows a uniform cell slide to be obtained without contamination of the cells by preservatives, workers or outside materials. The transfer from collection container to the cytology collection apparatus may be carried out without pouring or pipetting the collected specimen.

The present invention is directed to a cell collection and distribution apparatus that can be disassembled to allow face to face transfer of cells from the device to a slide for microscope examination. The present invention provides an improved apparatus and method for collecting a monolayer of cells that can be transferred to a microscope slide. The effectiveness of transferring the monolayer cells from the filter to a microscope slide has proven to be very high without differential cell loss. Microscopic examination shows that the cell distribution is the same on the slide as on the filter.

The devices of the present invention obviate the need for a trained technician to properly prepare a sample substrate. Thus, time, expense, and expertise are eliminated or reduced as critical factors in sample preparation protocols.

The devices and methods of the present invention also provide advantages in sample preparation because they are suitable for use with fresh, untreated cells, unmodified cells, and are particularly designed to provide a thin, uniform layer of solid matter (up to approximately 40 microns or more). This invention is particularly useful for collecting cells for a Pap smear.

The apparatuses and methods of the present invention have many advantages for conventional microbiology and hematology. The collected cells are in a predetermined area that is easily accessible to a radiant light source and to a wavelength absorbance meter. Because cells are concentrated in a single layer, they are almost always in one focal plane, thus eliminating or reducing interference by other particles and virtually eliminating technician time and expertise in establishing a proper reading. The minimal matter overlap achieved by the present invention ensures that all matter can be easily examined with little chance for critical solids to be obscured by clumps of overlapping solids or debris. Certain embodiments of the apparatuses of the present invention may be used in combination with other automated devices to detect and analyze any solid matter in a given population. They also permit a detailed analysis of the chemical composition of the matter.

The present invention also includes an improved apparatus and method for processing a fluid containing particulate matter. The apparatus and method include dispersing particulate matter in the sample, preferably by rotating the sample container around a fixed agitator or by rotating the agitator inside a fixed sample container. The present invention agitates the sample within the container to ensure break-up of large particulate matter, e.g., mucoid bodies in the case of sputum samples, and the even distribution of cells throughout the fluid. Agitation may occur as the result of relative motion between components of the sample container, non-uniform motion of the sample container, and/or inertial reaction forces applied to the sample by the container.

According to a preferred embodiment of the present invention structures and means are provided for rotating an agitator in relation to the container and/or the sample in the container. As described in more detail below, a preferred embodiment according to the present invention may include a cover within a cover, wherein the agitator is fixed to a freely rotatable outer cover and an inner cover is secured with respect to a stationary sample container. Such relative motion moves the agitator in relation to the sample, and disperses particulate matter in the fluid.

Further, providing a container cover that has a portion that is rotatable permits particulate matter stirring or dispersion without inserting a stirring mechanism into the sample, thus eliminating a source of contamination that plaques devices that are presently commercially available. In preferred embodiments of the present invention, the covering on the sample container may include a hollow tube, with or without a rotatable dispersing element, for withdrawing the sample from the container.

In a preferred embodiment of the invention, the cover comprises a first portion that fixedly engages the container and a second portion that may be rotatable in relation to the container. As used herein, rotatable in relation to the container refers to the relative movement of the first portion and the second portion; the first portion may be fixed and the second portion moveable, or the first portion may be moveable and the second portion fixed. In a most preferred embodiment, the second or inner portion of the cover is stationary and the first or outer portion is rotatable. In a preferred embodiment of the invention, the agitator is engaged by or fixed to the second portion of the cover.

An apparatus according to a preferred embodiment of the present invention may be configured to support, engage, and rotate a portion of a collection container so that the sample is mixed according to the present invention. An exemplary collection container includes a container or cup suitable for collecting and holding a specimen sample, a cap having a first position that is not rotatable in relation to the container and a second position that is rotatable in relation to the container, and an agitator engaged by or fixed to a portion of the cover and extending into the container. As used herein, configured to support, engage, and rotate refers to various configurations that may be adapted to perform the specific function. For example, an apparatus according to the invention may include a container support for positioning at least one sample container and rotating the container per se, and a sleeve or clamp for engaging and fixing a portion of the cap that communicates with an agitating element. Alternatively, the support may hold the container in a fixed position and a pulley, sleeve, or clamp may engage and rotate the portion of the cap that is fixed with respect to an agitator. In a preferred embodiment of the invention, a sleeve engages an inner portion of the cap, and holds the inner portion of the cap in a stationary position in relation to an outer portion of the cap.

Configurations or structures that engage a portion of the cap or the container typically include any member that positions, fixes and/or moves either that portion of the cap or the container. Exemplary members include, but are not limited to, a sleeve, one or more belts, one or more pulleys, one or more resilient bands, and the like.

The present invention is also a device for processing a fluid into one or more components, typically by removing particulate matter from the fluid. The present invention is directed to apparatuses and methods for collecting fluids, such as biological, physiological, or environmental fluids, and removing particulate matter from the fluid, without centrifugation, and diagnosing and testing the matter. In a preferred embodiment of the invention, particulate matter is collected on a collection site. In a most preferred embodiment of the invention, the particulate matter is collected in a monolayer and in a pre-determined spatial arrangement.

While a cytology collection apparatus according to the invention can be used for any biological fluid, it is particularly useful for preparing testing samples from urine and its associated cells for Pap smears. It is intended that the type of matter being processed should not limit the invention. In a most preferred embodiment of the invention, the fluid is urine and particulate matter is a cell. The particulate matter processing apparatus of the present invention also permits isolation and collection of fresh cells and/or microorganisms from biological fluids to perform DNA probe and chromosomal analysis once the proper buffer hemolyzes the cells.

In the case of cervical examinations, a scraping of the cervix is taken with a long-handled brush or broom. The handle is then shortened, such as by breaking or telescopic movement, and the brush is inserted into a specimen container. Conventionally, the container must be opened to remove the brush at the time of testing. Such a process increases the likelihood of contamination because the cover of the sample container must be opened, the brush typically retains cells if the testing is not performed soon after cell collection, and the operator must come into contact with the sample.

According to a preferred embodiment of the present invention, these problems are avoided by providing a system in which the brush not only remains in the collection container, but can also be used to disperse the collected cells during agitation. Further, the apparatus of the present invention is a closed system; once the apparatus is closed, it does not need to be opened in order to process any cells collected on the brush.

Further, providing a container cover that has a portion that is rotatable permits particulate matter stirring or dispersion without inserting a stirring mechanism into the sample, thus eliminating a source of contamination that plaques devices that are presently commercially available.

The present invention is also directed to a cytology collection and testing kit containing a cytology collection apparatus, replacement filters, replacement disposables, and/or other components, ingredients of a fixative composition as described below. The cytology collection kit may also include replacement filters, replacement disposables, and/or other components, ingredients or solutions typically used during cytological examinations. The kit might also include washing, fixative, and/or buffer solutions. A cervical kit may include a brush or broom, and a fluid suitable for storing the used brush until particulate matter on the brush can be processed through the filter assembly.

According to another aspect of the present invention, the matter collection apparatus may also include additional modules, removable or integrated, for treating the fluid. For example, the fluid may be treated with a matter collection module, in combination with a debris removal module, a chromatography module, and assay module, or combinations of these and other devices. These and other modules or treatment protocols provide features that may be desirable to incorporate into a sample preparation apparatus according to the invention.

The devices and methods of the present invention have many advantages for conventional cytology. The cells are in a predetermined area allowing for significant timesaving when screening the slide. Such problems as cells lying outside the coverslip or on the frosted end are eliminated. Because cells are lying in a single layer, they are almost always in a one focal plane when using a 10X objective—the objective most often used for the lower power screening of a slide. Even with a 40X objective, most cells are in focus. This eliminates frequent refocusing and saves time.

The objects of the present invention are achieved by an apparatus for simultaneously processing a positive whole number of samples wherein each of the samples includes a fluid containing a respective particulate matter. The apparatus comprises a number of containers corresponding to the number of samples, each of the containers being adapted for holding a respective sample; a number of pumps corresponding to the number of samples, each of the pumps being adapted for communicating a respective fluid with a respective container; a number of filters corresponding to the number of samples, each of the filters being interposed between a respective pump and its respective container and being adapted for collecting a respective particulate matter; a first engagement supporting each of the containers, the first engagement having a number of first receivers corresponding to at least the number of samples, each of the containers being contiguously engaged by a respective first receiver; and a second engagement retaining the pumps, the second engagement having a number of second receivers corresponding to the number of first receivers, each of the pumps being contiguously engaged by a respective second receiver. Relative movement between respective ones of the first and second receivers disperses a respective particulate matter in its respective fluid.

The objects of the present invention are also achieved by a method for simultaneously processing a number of samples wherein each of the samples are held in a respective container and include a respective fluid containing a respective particulate matter. The method comprises closing each of the containers with a respective pump, each pump including a respective filter being interposed between its respective container and its respective pump and being adapted for collecting its respective particulate matter; supporting each of the containers on a first engagement, the first engagement having a number of first receivers corresponding to at least the number of samples, each of the containers being contiguously engaged by a respective first receiver; retaining the pumps on a second engagement, the second engagement having a number of second receivers corresponding to the number of first receivers, each of the pumps being contiguously engaged by a respective second receiver; and moving respective ones of the first receivers relative to respective ones of the second receivers for dispersing its respective particulate matter in its respective fluid.

The accompanying drawings show illustrative embodiments of the invention from which these and other of the objectives, novel features and advantages will be readily apparent.

DESCRIPTION OF THE INVENTION

Figure 1:
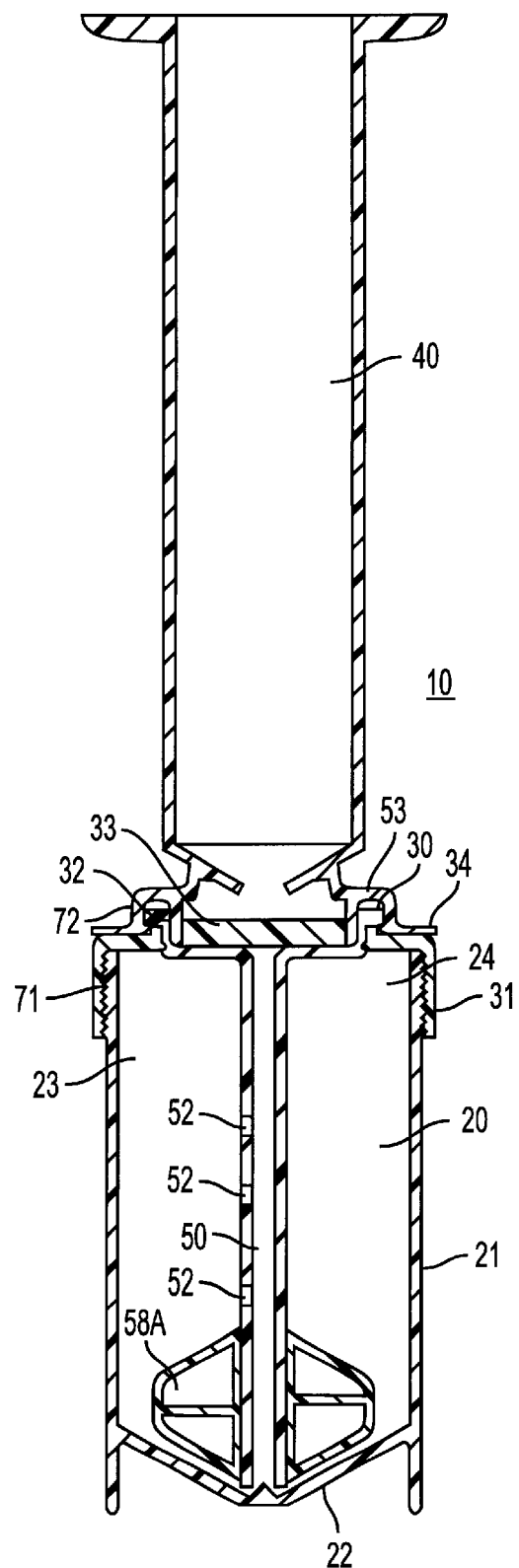
FIG. 1 is a cross section view of a first preferred embodiment of the present invention.

The present invention is a specimen container that includes a particulate matter separation chamber or module in fluid communication with a specimen container.

The present invention is also a device for processing a fluid into one or more components, typically by removing particulate matter from the fluid.

The present invention also includes devices and methods for collecting fluids, such as biological, physiological, or environmental fluids, removing the desired particulate matter from the fluid, without centrifugation, and diagnosing and testing the particulate matter. In a preferred embodiment of the invention, particulate matter is collected on a collection site. In a most preferred embodiment of the invention, the particulate matter is collected in a monolayer and in a pre-determined spatial arrangement.

The present invention also includes an improved apparatus and method for processing a fluid containing particulate matter. The apparatus and method include passing the fluid through a particulate matter separation chamber having a seat for a porous filter arrangement, the seat includes structures for aligning the collected particulate matter in a pre-determined spatial arrangement, structures that enhance the fluid flow through the particulate matter separation chamber, and/or structures that promote or retain the porosity and/or compression of the porous filter arrangement housed in the particulate matter separation chamber.

The present invention is also an improved device for collecting a processing a fluid, typically a biological fluid. The device includes a particulate matter separation chamber having one or more of the following: a collection site; a porous filter arrangement including a membrane for separating particulate matter from a fluid and a porous support frit; the porous filter arrangement establishes at least two fluid flow paths through the particulate matter separation chamber; a chamber seat that configures the collected particulate matter in a predetermined spatial arrangement; a particulate matter separation chamber having a concentric channel; a channel having one or more resilient members; a chamber seat having one or more resilient members; a chamber seat or base having posts; a chamber seat having one or more predetermined surface modifications; a chamber seat having one or more elements that promote a predetermined spatial arrangement of particulate matter on the collection site; and structures that enhance the fluid flow through the particulate matter separation chamber.

A device according to the present invention may also include structures that are configured for and/or are adapted to mix the specimen collected in the specimen container. Exemplary structures include, but are not limited to, a specimen container having a cap, or a portion of the cap, that is relatively rotatable; a cap or cap portion that is moveable in relation to the specimen container; and a tube or the like that extends into the specimen container. The tube may include one or more elements for agitating the specimen. The cap may also include a portion that fittingly engages a portion of a cover for particulate matter separation chamber in a liquid tight seal. The cap may also include a portion that fittingly engages a portion of the cover in a liquid-tight but not fluid-tight seal.

A device according to the invention may also include a pump or syringe. The pump or syringe may optionally include one or more elements configured to permit a predetermined amount of fluid into the pump or syringe.

The present invention also includes preparing a specimen for microscopic examination by processing a fluid using a device according to the invention, and collecting particulate matter on a collection site in the device.

The present invention also includes a method for analyzing matter comprising collecting a fluid in a chamber, collecting particulate matter on a collection site, and transferring the particulate matter collected on the collection site to a microscope slide or the like. Preferably, both collecting steps occur within the chamber.

A device according to the present invention may also include one or more separable elements. In a preferred embodiment of the invention, the device includes a separable particulate matter separation chamber. In a most preferred embodiment of the invention, the device includes a porous filter arrangement at least partially retained in a top portion of the chamber.

The present invention also includes a kit having an assay module that includes a particulate matter collection element according to the invention, a fluid specimen container, and a pump for inducing fluid flow from the specimen container through the assay module.

In a preferred embodiment of the invention, a fluid specimen in a container is in fluid communication with a particulate matter separation chamber or module for separating particulate matter in the fluid and collecting the separated particulate matter in a collection site. In a most preferred embodiment of the invention, the separated particulate matter is collected in a monolayer on the collection site. A preferred embodiment of the invention also includes a hollow tube providing fluid communication between the specimen container and the particulate matter separation chamber. More preferably, the hollow tube includes means for agitating the specimen and/or dispersing the particulate matter in the specimen.

In another embodiment of the invention, the apparatus includes the specimen container and particulate matter separation chamber described above, and a pump, syringe or the like. In this embodiment of the invention, various structures provide a fluid flow path from the specimen container, through the particulate matter separation chamber, and into the pump or syringe.

As used herein, the terms "sample" or "specimen" refer to any fluid in combination with solid matter, such as particulate matter, and from which it may be desirable to collect the particulate component from the sample for the purpose of establishing its identity or presence in the sample. Typically, the fluid component of the sample will be a liquid. However, the fluid may also be air or gas. As an example, it may be desirable to determine the presence of cancer cells or certain proteins in the biological fluid, such as urine. In another example, it may be desirable to evaluate the nature of contaminants, such as molecular contaminants, in ultra-pure water used in the electronics industry. Other exemplary fluids include but are not limited to body fluids, such as blood, spinal fluid, or amniotic fluid; bronchial lavage; sputum; fine needle aspirates; ground water; industrial processing fluids; and electronic or medical dialysis fluids, to identify just a few. It is intended that the type of fluid being processed should not limit the invention.

As used herein, the term "fluid" refers to any fluid for which it may be desirable to collect a component of the fluid for the purpose of establishing its identity or presence in the fluid. Typically, the component in the fluid will be a solid matter, such as particulate matter. For example, the fluid may be air or gas, or a biological fluid, such as urine, and it may be desirable to determine the presence of cancer cells or certain proteins in the biological fluid. In another example, it may be desirable to evaluate the nature of contaminants, such as molecular contaminants, in ultra-pure water used in the electronics industry. Other exemplary fluids include but are not limited to body fluids, such as blood, spinal fluid, or amniotic fluid; bronchial lavage; sputum; fine needle aspirates; ground water; industrial processing fluids; electronic or medical dialysis fluids; to identify just a few. It is intended that the type of fluid being processed should not limit the invention.

As used herein, the term "particulate matter" refers to any substance in a fluid that is capable of collection and evaluation, preferably by cytological examination. Exemplary particulate matter includes, but is not limited to cells or cell fragments, proteins, molecules, polymers, rubbers, stabilizers, antioxidants, accelerators, silicones, alkyds, thiokols, paraffins, thermoplastics, bacteria, pesticides, and herbicides. Specific exemplary polymeric matter include, but is not limited to polyethylene, polypropylene, polyisobutylene, polyacrylonitrile, polyethylene glycol, polyvinylchloride, polystyrene, polysulfide, polymethylmethacrylates, polyethyleneterephthalates, bisphenol A (a common environmental contaminant), ethyl cellulose, nitrocellulose, polyurethane, and nylon. Specific exemplary biological matter includes cancer cells, including distinguishing between metastatic and normal cancer cells; proteins, nucleic acids, antibodies, or the like.

As used herein, the terms "adapted for communication", "communicating," or similar terms refer to any means, structures, or methods for establishing fluid flow through the system, as are well known by practitioners in the art. Exemplary structures are shown in the Figures. For example, a conduit may have a connector adapted to receive or connect to a mated connector on another conduit. As used herein, the term "connector" refers to any structure used to form a joint or to join itself to another piece. These connectors or connections establish a fluid flow path through various elements of the apparatus, assembly, or system. Typical connections include but are not limited to mating connections, such as Luer-type, screw-type, friction-type, or connectors that are bonded together.

As used herein, "adapted for engaging", "engagement", "engaging", or similar terms refers to complementary structures that may align, mesh, mate, or rest near, against, or within each other. Exemplary structures include the connectors described above.

A device 10, according to an exemplary embodiment of the present invention that is shown in FIG. 1, includes a specimen container 20 holding a fluid specimen 23, a particulate matter separation chamber 30 having a porous filter arrangement, and a pump 40. FIG. 1 also shows a hollow tube 50 that includes a dispersing element 51.

Each of these elements will now be described in more detail.

The Collection Container

In accordance with the invention, specimen container 20 includes any container suitable for holding a fluid 23, preferably a biological fluid. The typical container includes sidewalls 21 and a bottom wall 22 that, in combination, contain the specimen 23. The specimen container 20 also has an open end 24 for collecting, holding, or storing the fluid 23. Typical fluids include, but are not limited to biological fluids, such as body fluids, wastewater fluids, or the like. Typical body fluids include urine or other biological fluids, such as blood, cerebrospinal fluid (CSF), bronchial lavage, sputum or fine needle aspirates.

The configuration and materials used to make the container (and any of the elements that comprise a device according to the invention) can be any of a variety of materials, shapes, and sizes. For example, the cup can be constructed of any material compatible with the fluid to be processed. It will be appreciated that the container and the assembly of the sidewalls to the bottom wall can be any conventional assembly. In a preferred embodiment of the invention, bottom wall 22 is a conical member, as shown in FIG. 1. Optionally, bottom wall 22 or sidewall 21 may include one or more fins or the like (not shown) extending into the interior of container 20. Such fins may be desirable an embodiment of the invention described in more detail below in which the sample in the container is agitated by rotation of the container.

Figure 2:
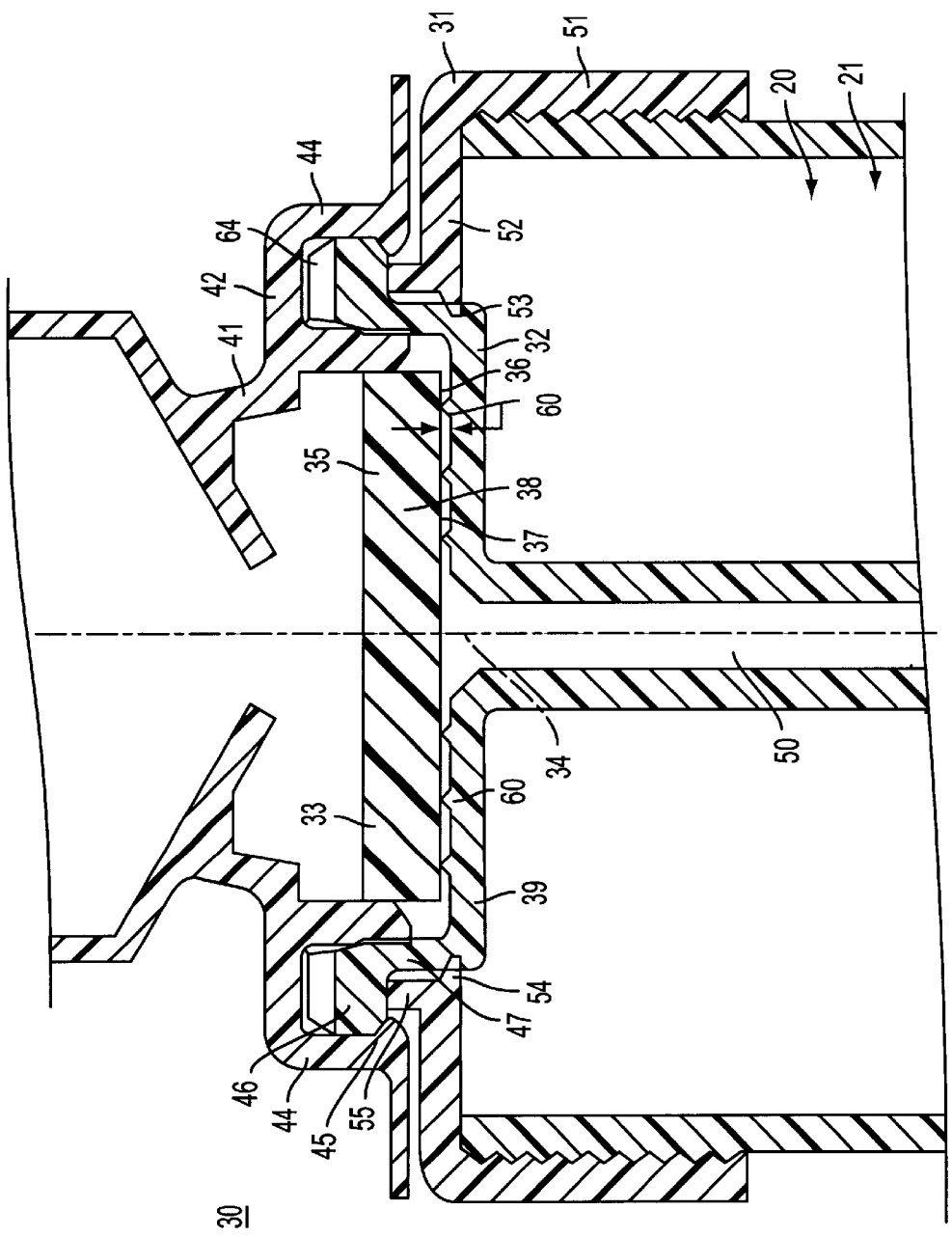
FIG. 2 is a cross section view of the particulate matter separation chamber according to the present invention.

As shown in FIGS. 1 and 2, a device according to the invention also includes a cap 31. In a preferred embodiment of the invention, the cap 31 is configured or adapted to receive a lower portion 32 of a particulate matter separation chamber 30. The cap 31 may be variously configured to achieve the desired function. A preferred embodiment is shown in FIG. 2. The cap 31 may include a downwardly extending member 51 configured to engage sidewall 21 of container 20. It is intended that cap 31 may be any configuration or shape that closes or seals open end 24 of container 20.

The cap also includes portion 52 having an opening adapted to receive the lower portion 32 of the particulate matter separation chamber 30. Although the engagement between cap portion 52 and lower portion 32 may be variously configured, lower portion 32 preferably includes a groove 53 adapted to receive a projection 54 from the opening in cap portion 52. In a most preferred embodiment of the invention, the engagement is a snap fit, with the engagement between lower portion 32 and the projection 54 permitting lower portion 32 to rotate relative to cap portion 52. This configuration is preferably liquid tight, and in a most preferred embodiment of the invention, the seal is liquid tight, but not gas (e.g., air) tight.

A preferred configuration for the cap 31 will now be described with respect to FIG. 13. The cap 31 may be variously configured to achieve the desired function. According to this embodiment of the invention, cap 31 includes structures and means for allowing an outer cap 71 to move in relation to an inner cap 72. Outer cap 71 is preferably fixed to and/or in fluid communication with tube 50. In a preferred embodiment of the invention, the outer cap 71 and tube 50 are relatively rotatable with respect to inner cap 72, when inner cap 72 is tightened on container 23. Such relative motion between outer cap 71 and inner cap 72 moves sample in the container 23 in relation to agitator 58A (FIG. 1), brush 58B (FIG. 10) or broom 58C (FIG. 11).

In the embodiment of the invention that includes the inner and outer caps, it is preferred that the inner and outer caps are adapted to engage each other so that the respective caps do not rotate until the final closing of the cap on the container. It is intended that at least initially, the respective caps act as a unitary cap. When the cap unit is tightened to a pre-determined position, however, it is intended that any structures holding inner cap 72 in place in relation to the outer cap 71 be broken or released so that inner and outer caps rotate freely with respect to one another. For example, inner cap 72 may be used to seal the container and outer cap 71 may snap fit over the inner cap 72. In this embodiment of the invention, a tab or the like on the inside of the outer cap 71 may prevent relative movement between the inner and outer caps when the respective caps are in a first position. Moving the outer cap 71 to a second position, e.g., breaking the tab, permits rotation of the outer cap 71 relative to the inner cap 72. Alternatively, it is envisioned that a temporary spacer (not shown) would initially maintain the inner and outer caps at an axially spaced apart position. After tightening the inner cap 72 on to container 20, the spacer would be removed and the outer cap 71 slid axially over the inner cap 72 to a position that is freely rotatable with respect to the inner cap 72.

An alternative or additional structure in the embodiment of the invention that includes a cover with a flexible wall 55, preferably circular or elliptical, that engages and or supports a portion 45 of the particulate matter separation chamber 30.

In a most preferred embodiment of the invention, the wall 55 includes one or more spaced apart notches (not shown). It is intended that these notches provide a degree of flexibility in the wall so that, if desired, the lower portion of the particulate matter separation chamber 30 can be disengaged from the cap 31 (see, for example, FIG. 5).

Figure 5:
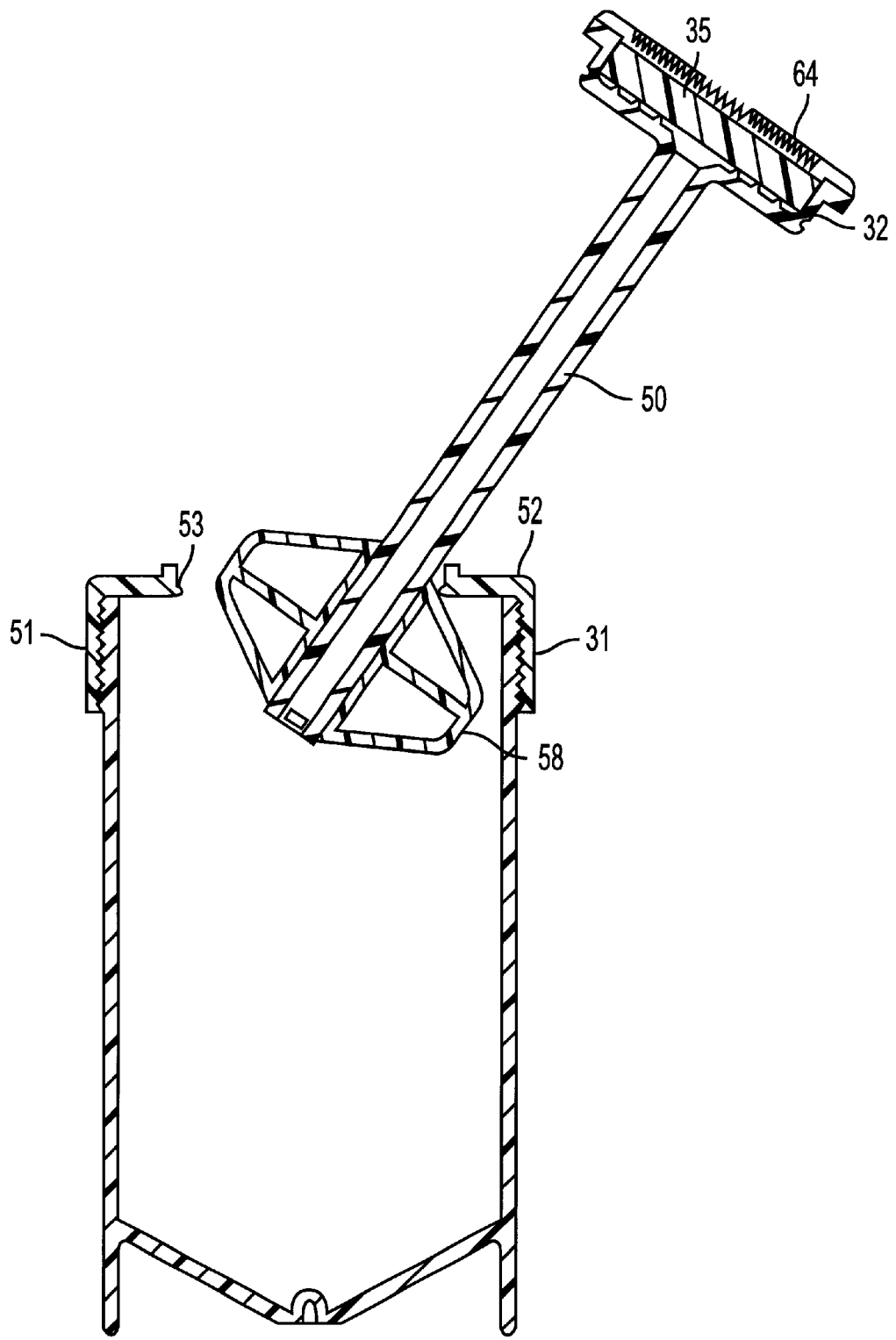
FIG. 5 is a cross section view of a disassembled base, hollow tube, and container.

FIG. 5 also illustrates another embodiment of the invention relating to a cap 31 having a slot through which the agitator 58A or broom 58C can be positioned inside the container 20. In a preferred embodiment of the invention, the slot or opening in the cap 31 can be covered with a removable and/or penetrable covering that protects the inside of the container 20 from contamination until the container 20 is ready for use. For example, a brush 58B or the like can be used to collect a cervical sample, the covering can then be removed from the cover 31, and the brush 58B can be placed in the container 20.

According to another preferred arrangement, the inner cap 71 may have a collar (not shown) that coaxially circumscribes tube 50 and extends partially into the container 20. Such a collar redirects the specimen 23 back down into the container 20 during agitation, such as would occur during vortex agitation. This is advantageous insofar as the collar imposes little or no resistance to relative rotation between the inner cap 71 and the outer cap 72. Moreover, it is envisioned that the outer cap 72 may have formed thereon a mating nipple for attaching the tube 50. The mating nipple may be formed on the outer cap 72 so as to extend coaxially within the collar. In this way, a telescoping or breakable tube 50 may be used in its elongated configuration to collect the specimen, and then reconfigured to its collapsed configuration and attached to the mating nipple. Such an arrangement according to this embodiment would further reduce the possibility of sample contamination by minimizing handling of the specimen between the time the sample is collected and the time it is examined.

Particular Matter Separation Housing

In accordance with the present invention, a device according to the invention includes a particulate matter separation housing that may be variously configured. An exemplary configuration is shown in FIG. 2. Any housing 30 adapted to receive a particulate matter collection assembly 33 may be used.

As shown in FIGS. 1 and 2 the particulate matter separation chamber 30 is preferably a two piece housing formed by a top portion 41 and base portion 32. In a preferred embodiment of the invention, top portion 41 releasably engages base portion 32; however, alternative chamber configurations or assemblies that providing access to the porous filter arrangement 35 are suitable. In a preferred embodiment of the invention, base portion 32 includes a side wall 47, typically circular, that optionally includes a serrated portion 63 (shown in FIG. 4A) that engages or communicates with side wall 44 and seat 42 of top portion 41. It has been found that the optional serrated portion 63 of the lower portion 32 facilitates disengaging the lower portion 32 from the top portion 41. Top portion 41 and base portion 32 may be connected or fastened to each other by any mating connection or means that provides a liquid or fluid tight fit, e.g., Luer-type (threaded or not threaded), screw thread-type, friction-type, a tapered mating connection, or snap fit (as illustrated).

Base portion 32 includes a side wall and bottom wall suitable for seating a particulate matter filter assembly 33. Base portion 32 may also include a central bore or aperture 34 communicating with the hollow tube 50. In a preferred embodiment of the invention, hollow tube 50 extends into specimen container 20. In a preferred embodiment of the invention, base portion 32 may be a separate structure that is capable of rotating with respect to the cap 31. In order to achieve ease of centrifugal rotation while maintaining a liquid-tight assembly, base portion 32 may matingly engage base 31 through a tongue and groove arrangement (see FIG. 2).

Figure 4A:
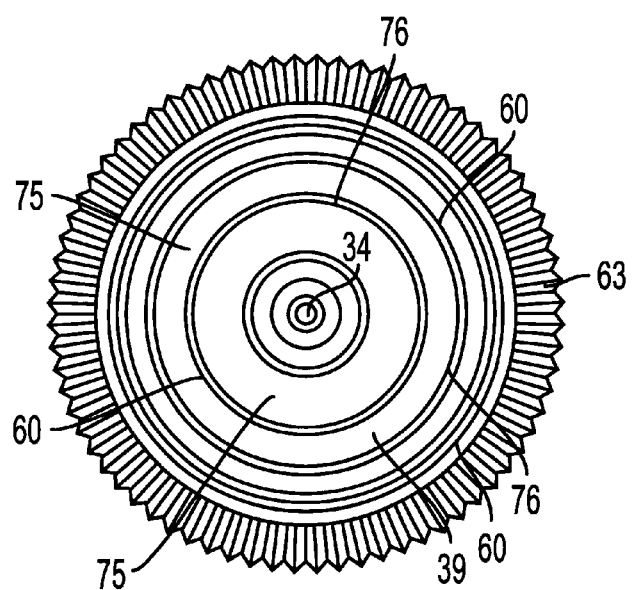
FIG. 4A is a top view of the base and well assembly, forming the bottom portion of the particulate matter separation chamber.
Figure 4B:
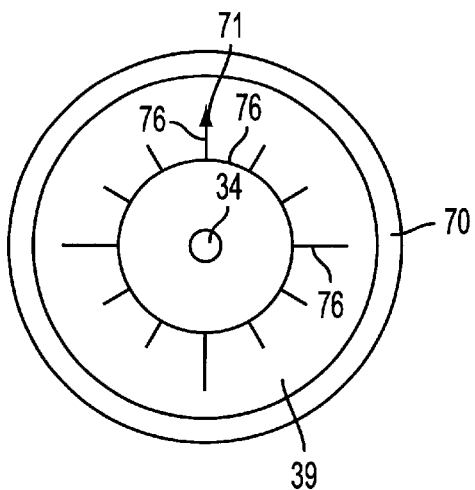
FIG. 4B is a top view of the bottom portion of the particulate matter separation chamber, and illustrates a clock face surface modification of the well.
Figure 4C:
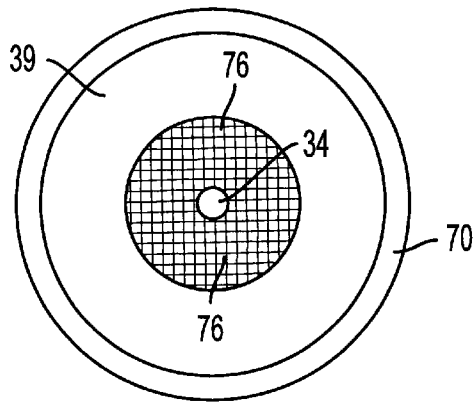
FIG. 4C is a top view of the bottom portion of the particulate matter separation housing, and illustrates cross hatch face surface modification of the well.
Figure 6:
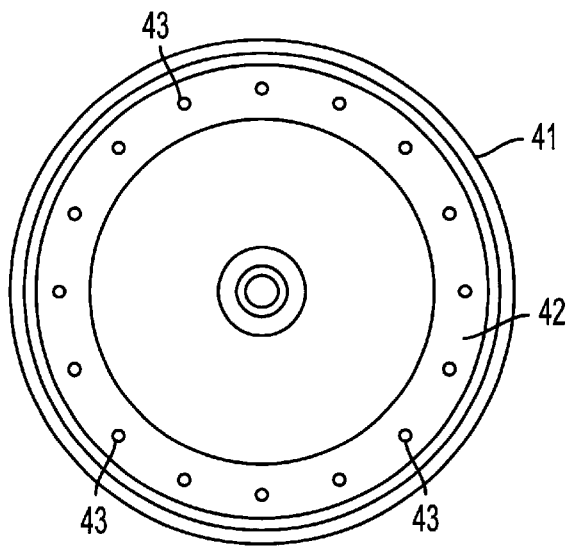
FIG. 6 is a bottom view of the top portion of the particulate matter separation housing.

In accordance with an embodiment of the invention, base portion 32 of the particulate matter separation chamber 30 housing includes a bottom wall or seat 39. As shown in FIGS. 4A–4C, seat 39 may include one or more spaced apart ribs or projections 60. Projections 60 are preferably of a configuration, size, and shape sufficient to prevent porous arrangement 35 flush contact with seat 39. In the embodiment shown in FIG. 4A, projections 60 are concentric rings.

Alternative configurations are described in more detail below. In a preferred embodiment of the invention, projections 60 function in one or more of the following ways: projections 60 may break the surface tension between porous filter arrangement 35 and seat 39 during use; when porous filter arrangement 35 is to be pulled away from seat 39, first porous medium 36 does not remain in contact with seat 39; projections 60 may evenly distribute pressure of the porous filter arrangement in the particulate matter separation chamber 30; projections 60 may prevent or suppress compression of the porous filter arrangement; and projections 60 may be configured to distribute any collected particulate matter in a pre-determined configuration or spatial distribution.

In accordance with the present invention, the surface of seat 39 may include one or more structures, configurations, or surface textures that promote the ability of the porous filter arrangement 35 to release from the seat 39, that promote a pre-determined spatial distribution of particulate matter on the collection site, and/or prevent or suppress compression of the porous filter arrangement 35. One embodiment of the invention includes concentric projections, such as projections 60 described above. Other configurations include, but are not limited to a grid, cross-hatching or the like, concentric squares or rectangles, or a series of continuous or separated structures, nubs, protuberances, granulations, or the like (see FIGS. 4B and 4C). It is intended that any element, structure, or chemistry that provides a texture to the surface of the seat 39 for accomplishing the above stated functions is suitable for use with the present invention.

In a preferred embodiment of the invention, the surface of the seat is configured into cross-hatching (see FIG. 4C). In another preferred embodiment of the invention, the surface of the seat is configured into a sundial or clock face structure (see FIG. 4B). Both of these embodiments, as well as other surface configurations disclosed herein, promote the collection of particulate matter on the collection site in a pre-determined spatial arrangement. The configurations shown in FIGS. 4B and 4C are particularly desirable because the imprint of the surface treatment of the seat may be transferred to the microscope slide and used to locate and identify specific particulate matter, such as a cancer cell, using a coordinate system. It has been found that a greater portion of particulate matter collects in regions on the collection site corresponding to or opposite areas 75 of the seat. Conversely, high spots 76 are regions that correspond to areas of where smaller amounts of particulate matter collects on the collection surface. These regions are imprinted on the microscope slide when the collection surface is placed in contact with the slide.

For example, a technician reading a microscope slide according to the present invention may be able to identify and locate a cell of interest by noting that the particular cell can be found at an angular position corresponding to 2 O'clock on the clock face configuration shown in FIG. 4B. Imprinting a microscope slide in such a manner significantly speeds reviewing slides and significantly improves the ability of a technician to find previously identified matter of interest. Included with the invention are one or more structures on the seat surface that provide positive orientation of the particulate matter as it is collected on the collection site and transferred to the microscope slide. For example, a suitable coordinate-identifying structure may be an arrow 71 or the like, as shown in FIG. 4B.

In accordance with another embodiment of the invention, the seat 39 and/or lower portion 32 may optionally include a channel 70 or the like, examples of which are shown in FIGS. 4B, 4C and 7–9. In a preferred embodiment of the invention, seat 39 slopes slightly outward toward the channel 70. The slight slope of the seat 39 and the channel 70 romote enhanced fluid flow through the particulate matter separation chamber 30 and decreases the surface tension of the seat 39 on the filter arrangement 35, both of which promote the capability of the porous filter arrangement 35 to disengage from the lower portion 32 of the particulate matter separation chamber 30. This aspect of the invention is another structure(s) that promote release of the porous arrangement.

Figure 7:
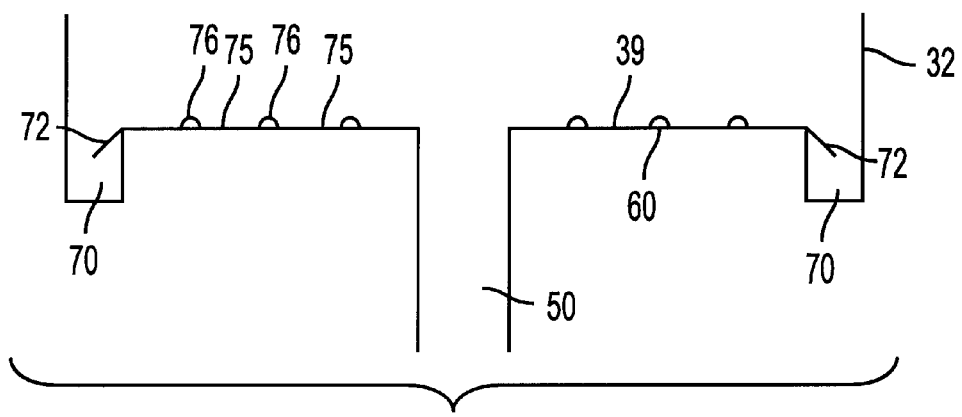
FIG. 7 is a cross section view of the bottom portion of the particulate matter separation housing, and shows the optional channel and optional flap.
Figure 8:
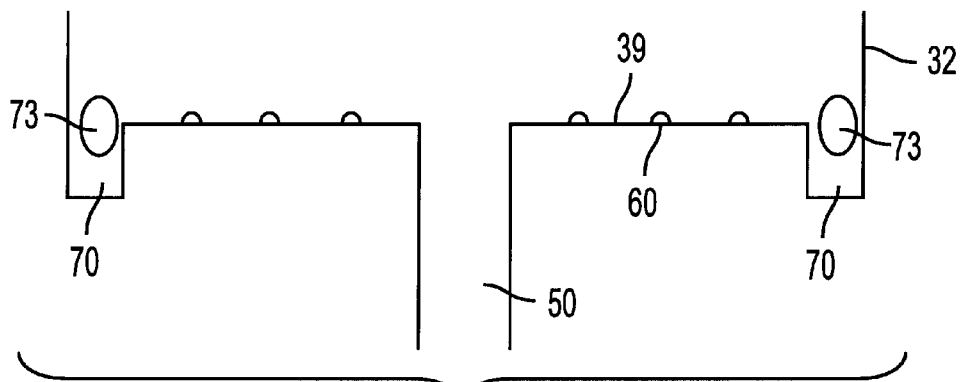
FIG. 8 is a cross section view of the bottom portion of the particulate matter separation housing, and shows the optional channel and optional O-ring.
Figure 9:
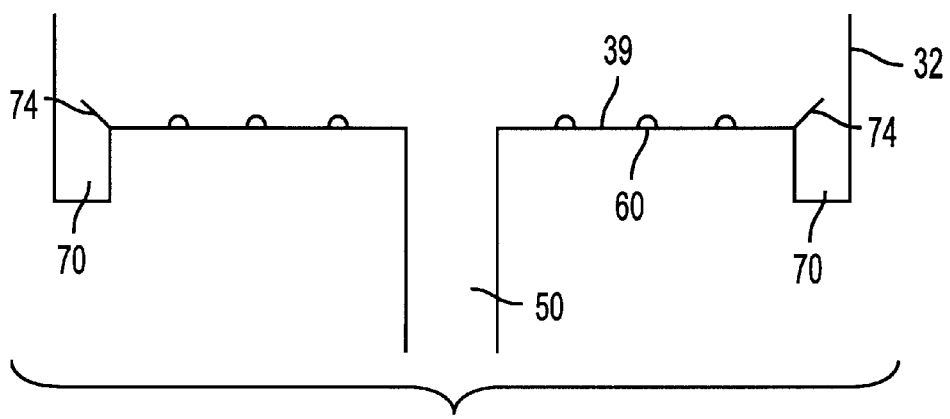
FIG. 9 is a cross section view of the bottom portion of the particulate matter separation housing, and shows the optional channel and optional flap.

Additional structures are shown in FIGS. 7–9 that address or are involved with promoting fluid flow through the particulate matter separation chamber 30 and also are involved in the release of the porous filter arrangement 35 from the lower portion 32. FIG. 7 shows flap 72 that extends downwardly into channel 70 from the lip of seat 39. FIG. 8 shows an O-ring 73 or the like that is positioned in the channel 70, preferably so that a top surface of the O-ring 73 is slightly above the plane of seat 39. This insures that O-ring 73 will engage a portion of porous filter arrangement 35 when positioned in the lower portion 32. FIG. 9 shows a flap 74 that extends upwardly from an outer portion of seat 39, insuring that flap 74 will engage a portion of porous filter arrangement 35 when positioned in the lower portion 32. In a preferred embodiment of the invention, flap 72, O-ring 73, and flap 74 are made of a resilient material. The preferred configuration is that shown in FIG. 9.

In accordance with the invention, the particulate matter separation chamber 30 is configured to receive a porous arrangement 35 having a particulate matter collection site 36 adapted to collect particulate matter as fluid containing the particulate matter passes through the chamber 30.

Porous arrangement 35 having a collection site 36 adapted to collect matter may be positioned across a fluid flow path, the collection site 36 communicating with hollow tube 50. The porous arrangement 35 within the matter separation chamber is preferably adapted to define at least one fluid flow path having first and second branches, the first branch 61 extending through the collection site 36 and the second branch 62 bypassing the collection site 36 (e.g., see FIG. 3).

In a preferred embodiment, the invention includes a porous filter arrangement 35 having a first porous medium 37, suitable for preventing the passage of particulate matter therethrough, and a second porous medium 38, suitable for allowing fluid to pass therethrough. The second porous medium 38 may or may not be capable of removing particulate matter from the fluid 23, a design choice according to the needs of a particular device. In a preferred embodiment, the first porous medium 37 is suitable for capturing or collecting particulate matter, and even more preferably, capturing or collecting particulate matter in a uniform or single layer. A preferred embodiment also includes a second porous medium 38 that is suitable as a support for the first porous medium 37.

The nature of the material used to make the porous media, the compatibility of the materials chosen for the porous media with one another and with the liquid to be processed are all factors to be considered in selecting a particular material for a porous medium for a given application.

Porous filter arrangement 35 may include a unitary structure having a first porous medium 37 of density and/or pore size suitable to prevent the passage of cells therethrough and a second porous medium 38 of density and/or pore size suitable for passing the fluid therethrough.

In a preferred embodiment, the porous filter arrangement 35 includes a first porous medium 37 comprising a porous polycarbonate membrane, suitable for preventing the passage of particulate matter therethrough. The porous filter arrangement 37 may further include second porous medium 38 comprising a depth filter or frit. The depth filter may be made of polypropylene or high-density polyethylene POREX® porous plastics. In a preferred embodiment of the invention, the second porous medium 38 may include a serrated or saw-tooth downstream portion 64, an example of which is illustrated in FIG. 2. It is intended that portion 64 is a structure and configuration that reduces or ameliorates compression of the porous filter arrangement 35 when it is positioned in the particulate matter separation housing 30.

It should be noted that various types of porous filter arrangements 35 could be used interchangeably with that of the present embodiment. While a polycarbonate membrane 37 is especially suitable for use in the cytology collection apparatus of the present invention, other porous membranes are also suitable. Exemplary porous membranes are disclosed in U.S. Pat. Nos. 5,471,994 and 5,301,685, which are incorporated by reference.

The porous membrane 37 preferably has a pore size from about 0.22 microns to about 8 microns, more preferably from about 1 micron to about 6 microns, most preferably about 2 microns, which allows it to trap particulate matter, e.g., cells, which are more than 3 microns in size. The membrane is suitable to allow fluid flow to pass therethrough while preventing the passage of particulate matter. The second porous medium 38 is suitable for passing fluid therethrough and may also be capable of removing particulate matter from the fluid 23. The pore size of the second porous medium 38 may range from about 5 microns to about 60 microns, preferably from about 15 microns to about 45 microns, most preferably about 35 microns.

As one skilled in the art will recognize, adjusting the pore size of the porous membrane 37 and the porous depth filter 38 in accordance with the type and/or size of matter to be collected permits the collection of the particulate matter on the collection site. In a preferred embodiment of the invention, the pore size is chosen so that a uniform layer of matter, preferably a monolayer of matter, is formed on the collection site. For example, from about 3 $\mu$m to about 40 $\mu$m or more has been shown to be effective, but it is intended that the invention should not be limited to a certain range of pore size.

In a most preferred embodiment of the invention, first porous medium 37 is attached to second porous medium 38 using an adhesive that is soluble in liquid. Such soluble adhesives include but are not limited to sugar compositions, gels, and the like.

The first porous medium 37 and the second porous medium 38 may be positioned in any fashion that functions as described herein. As one skilled in the art will recognize, the porous filter arrangement 35 may be variously configured and positioned as needed to achieve a particular result. For example, the first and second porous media may be separate, spaced apart media; the two media can be laminated together; the first medium can be integral with or removably engaged with the second porous medium; or the collection element may comprise a zone of higher density which mimics the function of the first porous medium as described above, and zone of lower density which mimics the function of the second porous medium as described above. Choice of these various configurations are well within the skill of practitioners in the art. Variations on the structure and composition of the porous arrangement will be described in more detail below.

Figure 12:
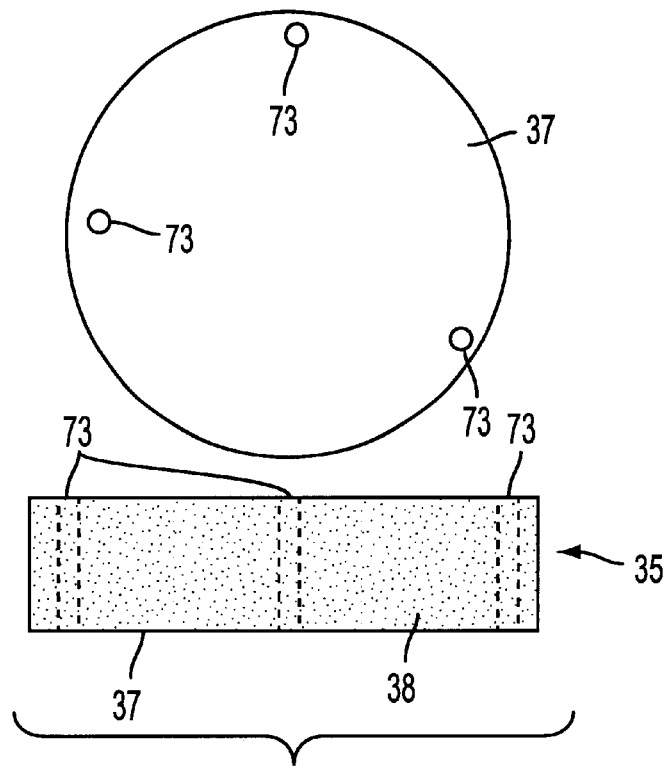
FIG. 12 is a combination of bottom and side views of a filter arrangement according to a preferred embodiment of the invention.

As shown in FIG. 12, a porous support 38 with at least one through bore 73, preferably a bore positioned near the circumference of the porous support 38, provides a direct conduit for suction so that a filter membrane 37 is retained on the porous support 38 when the particulate matter separation chamber 30 is opened to expose the membrane 37 for further processing.

In another embodiment of the invention, lower portion 32, tube 50, and fins 58 form an integral unit, and may be separated from cap 31 to facilitate removal of the integral structure from container 20. An exemplary structure of this embodiment of the invention is shown in FIG. 5.

Pump

In accordance with the invention, specimen container 10 includes a pump 40. In a preferred embodiment of the invention, pump 40 is a syringe or the like for altering differential pressure within the apparatus so that fluid can be drawn from the specimen container 20 through the particulate matter separation chamber 30.

In accordance with the present invention, the pump 40 may be variously configured. In a preferred embodiment of the invention, pump 40 includes an end that forms the cover portion 41 of the particulate matter separation chamber 30. Cover portion 41 includes a seat 42 or the like configured to engage a downstream portion of porous filter arrangement 35. In a preferred embodiment of the invention, the seat 42 positions porous filter arrangement 35 in the cover so that porous filter arrangement 35 does not move during use. In a most preferred embodiment of the invention, seat 42 includes a plurality of projections or posts 43 of a size, shape, and number to position the porous filter arrangement 35 in the particulate matter separation chamber 30, to promote substantially even distribution of pressure against the porous filter arrangement 35, and to reduce or prevent compression of the porous filter arrangement 35 that could interfere with fluid flow through the porous filter arrangement 35.

In a preferred embodiment of the invention, cover portion 41 removably engages bottom portion 32 to form the particulate matter separation chamber 30. Cover portion 41 may engage bottom portion 32 in any manner and with any structures that allow cover portion 41 to disengage bottom portion 32. In a preferred embodiment of the invention, illustrated in FIG. 2, cover portion 41 includes a downwardly extending side wall 44 having a flange 45 or the like adapted to releasably and/or resiliently engage a shoulder 46 or the like on bottom portion 32.

Movement of fluid through the collection apparatus may be effected by maintaining a pressure differential between a source of fluid and the destination of the fluid. Exemplary means of establishing this pressure differential may be by applying pressure to any part of the system on the inlet side of the particulate matter separation chamber 30 (e.g., the specimen container 20); applying a vacuum to any part of the system on the outlet side of the housing (e.g., the syringe 40); or any form of pump, such as an autovial spunglass filter (manufactured by Genex Corporation); gravity head; or a flexible, collapsible container, such as a specimen container, which may be squeezed to force fluid through the matter collection apparatus and into the syringe. In a preferred embodiment of the invention, a syringe draws fluid from a collection cup through the housing.

Hollow Tube

In accordance with a preferred embodiment of the present invention, specimen container 20 includes a tube 50 or the like for drawing fluid 23 into the particulate matter separation chamber 30. Typically, tube 50 will be hollow and open or openable at both ends. Tube 50 includes open end 51 near the bottom of the collection chamber 23, and may include one or more apertures 52 into tube 50. Open end 51 and/or apertures 52 permit different fluid layers as well as sediments to be simultaneously tested when the fluid is drawn into the particulate matter separation chamber 30.

In accordance with another embodiment of the improved invention, hollow tube 50 includes at least one projection or fin 58A or the like, as shown in FIG. 1. In a preferred embodiment of the invention, hollow tube 50 is rotatable and fin 58A stirs the liquid specimen, and in a most preferred embodiment, disperse cells and/or particulate matter, and/or to disrupt any large particulate matter such as mucoid bodies. In another preferred embodiment of the invention, hollow tube 50 and lower portion 32 are of unitary construction, and the lower portion 32, tube 50, and fin 58A are movable in relation to the specimen container 20. For example, if the container is rotated, optional fins in the side and/or bottom walls of the container may create concentric movement of the sample in the container, movement that will be disrupted by the presence of fin 58A. Alternatively, lower portion 32, tube 50, and fin 58A may be rotated within a stationary container.

Figure 10:
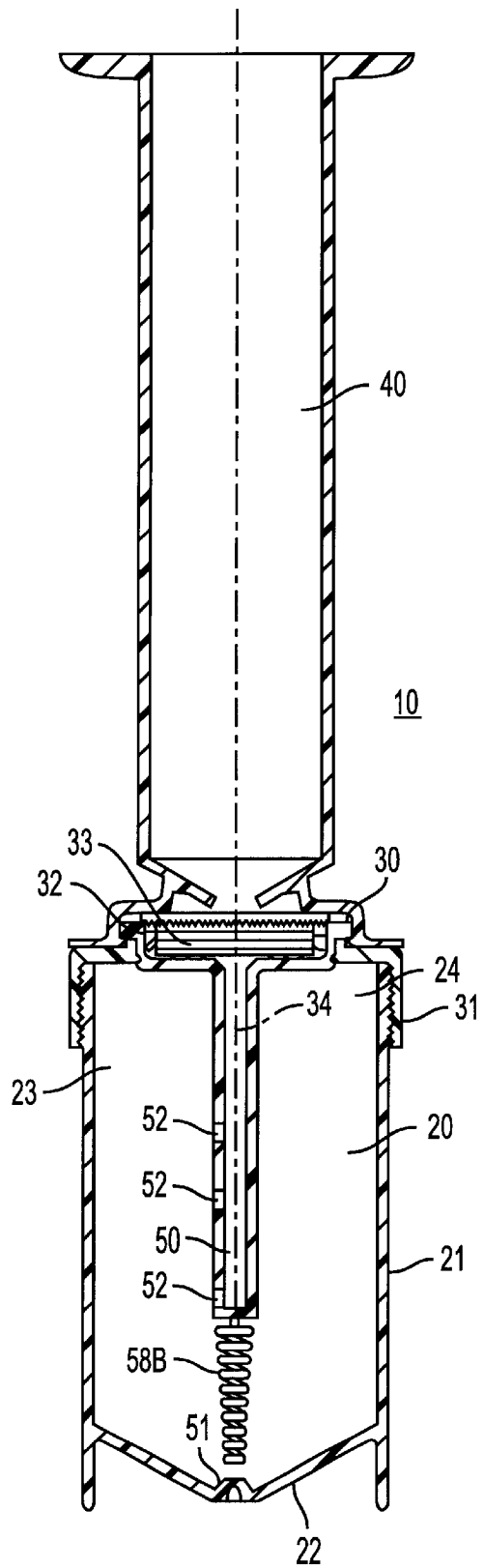
FIG. 10 is a cross section view of a second preferred embodiment of the present invention.
Figure 11:
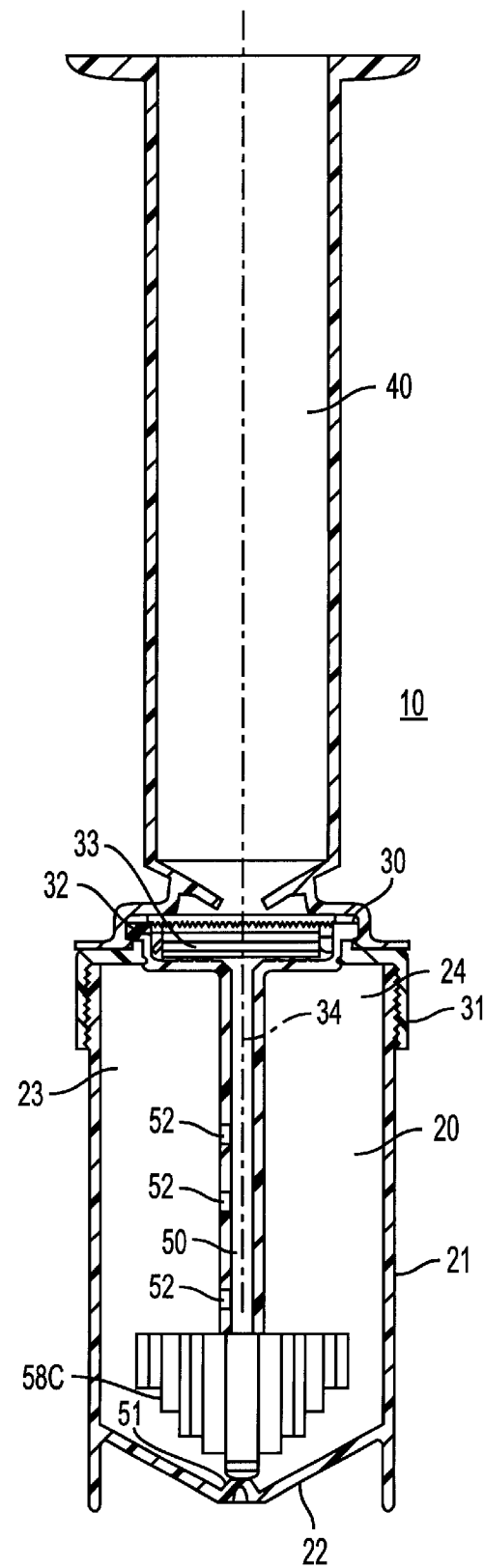
FIG. 11 is a cross section view of a third preferred embodiment of the present invention.

As shown in FIGS. 10 and 11, as an alternative embodiment of the invention, agitator 58 may comprise fibers, a brush, swab, or broom or the like. Preferably, such fibers or brush are suitable for dispersing particulate matter in the container when the sample is vortexed in relation to the agitator, brush, or broom. In a most preferred embodiment of the invention, the brush or broom is also suitable for use in collecting particulate matter from a patient, e.g., a cervical brush or broom or the like. It is intended that the brush can be fixed to a portion of the cap 31, or the cap 31 may include a slot, collar or the like for matingly engaging a portion of the handle at the opposite end of the brush.

Mixer

Figure 13:
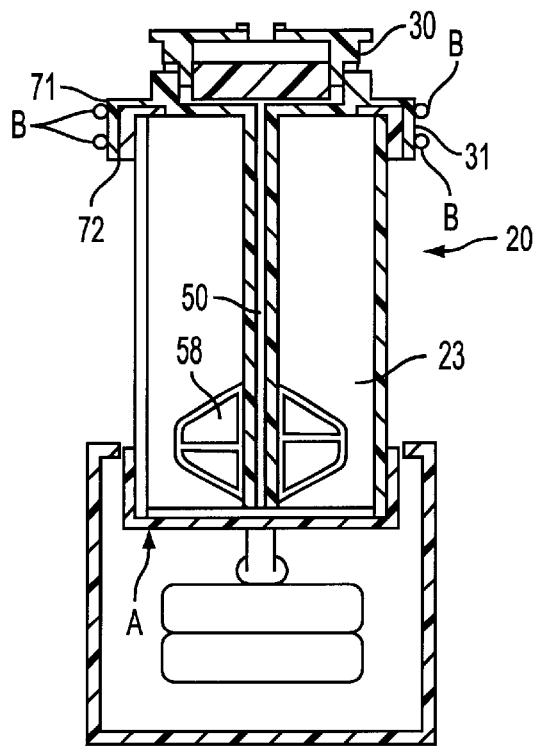
FIG. 13 is a cross section view of an apparatus used in a semi-automatic method according to a first preferred embodiment of the present invention.
Figure 14:
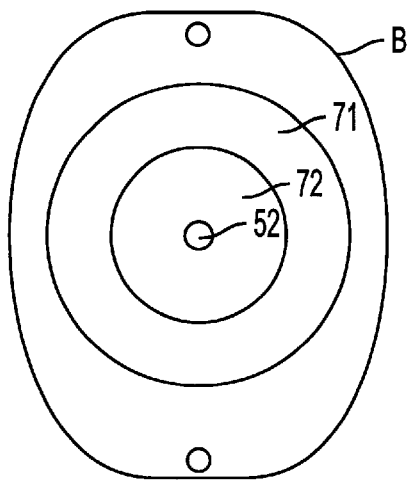
FIG. 14 is a schematic illustration of the apparatus shown in FIG. 13 in a first position.
Figure 15:
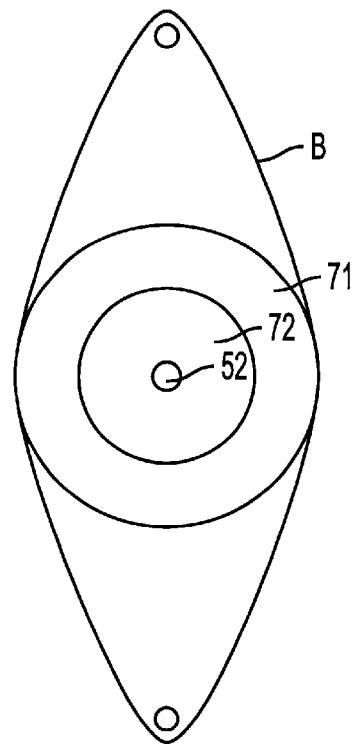
FIG. 15 is a schematic illustration of the apparatus shown in FIG. 13 in a second position.
Figure 16:
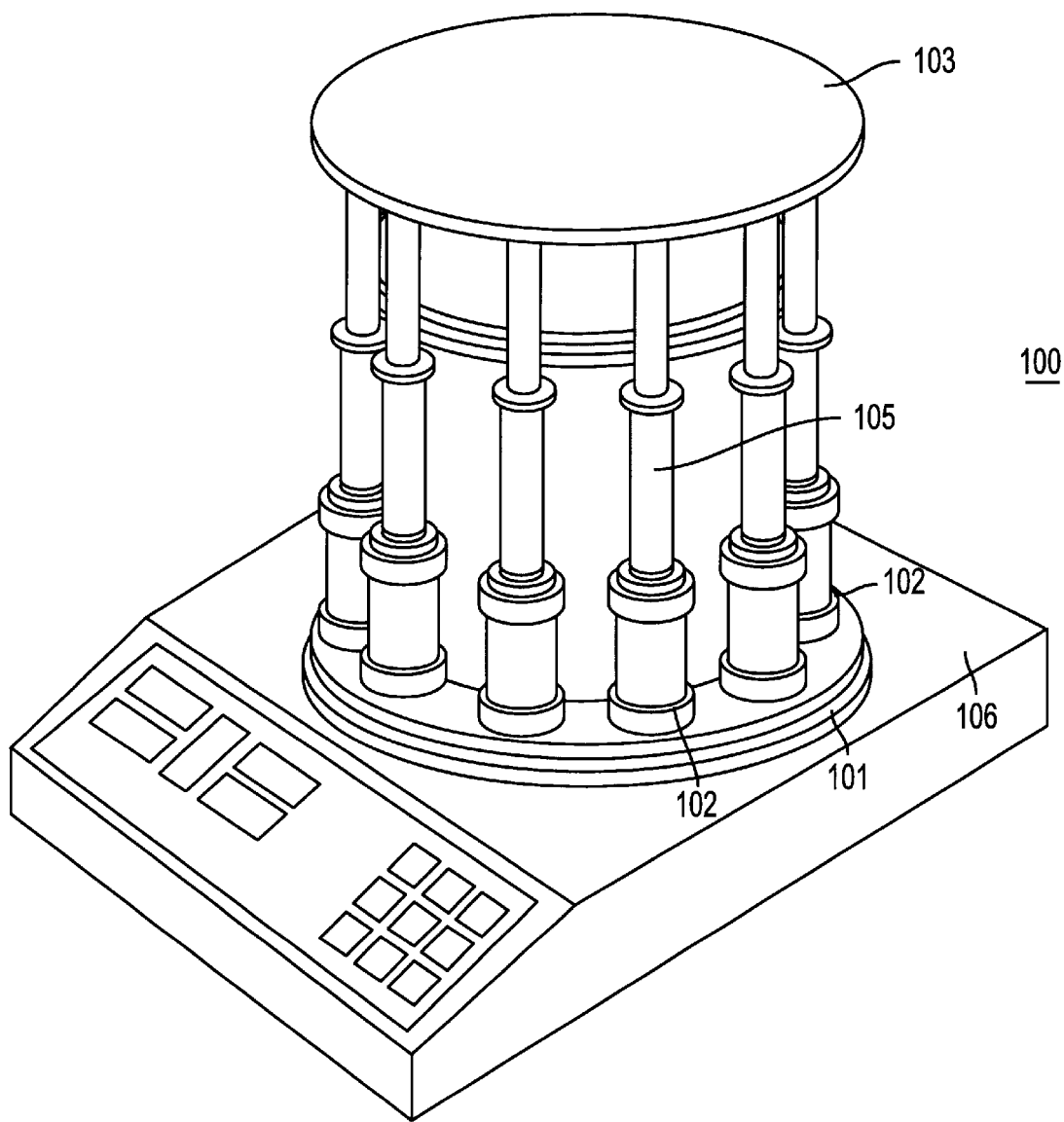
FIG. 16 is a rendering of a mixing apparatus used in a semi-automatic method according to a second preferred embodiment of the present invention. An upper platform of the mixing apparatus is shown in its upper or open configuration.
Figure 17:
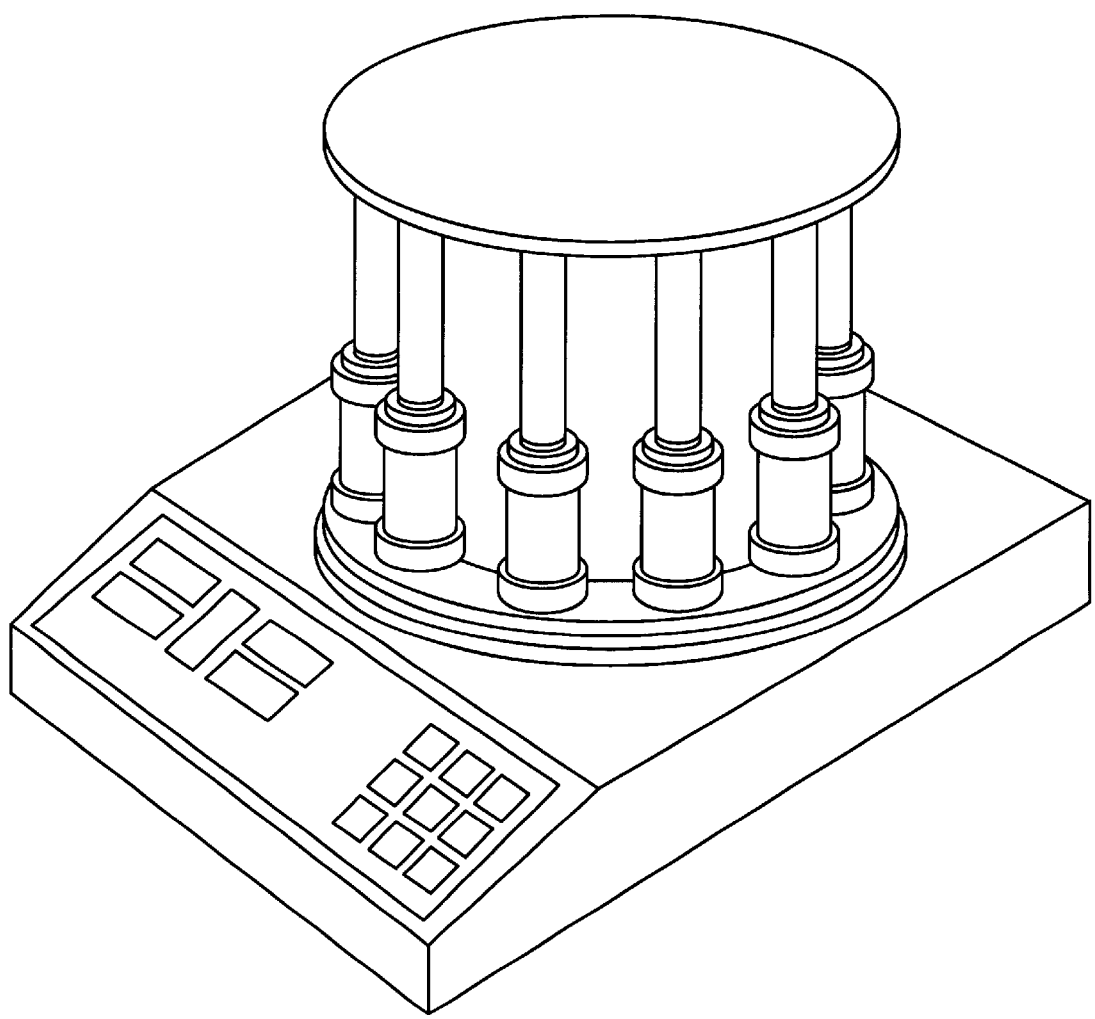
FIG. 17 is a rendering of the mixing apparatus shown in FIG. 16 showing the upper platform in its lower or closed configuration.
Figure 18:
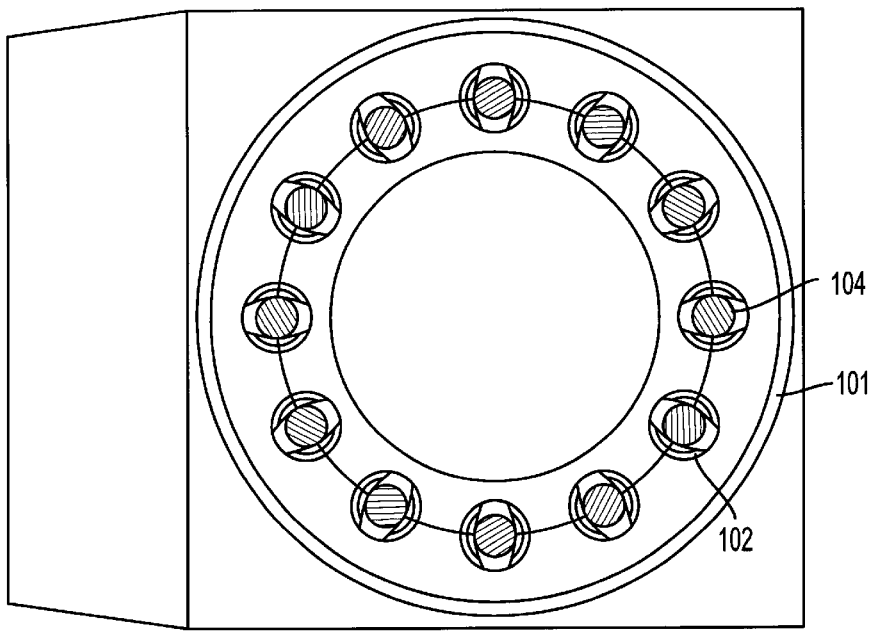
FIG. 18 is a top view of the mixing apparatus shown in FIG. 16.
Figure 19:
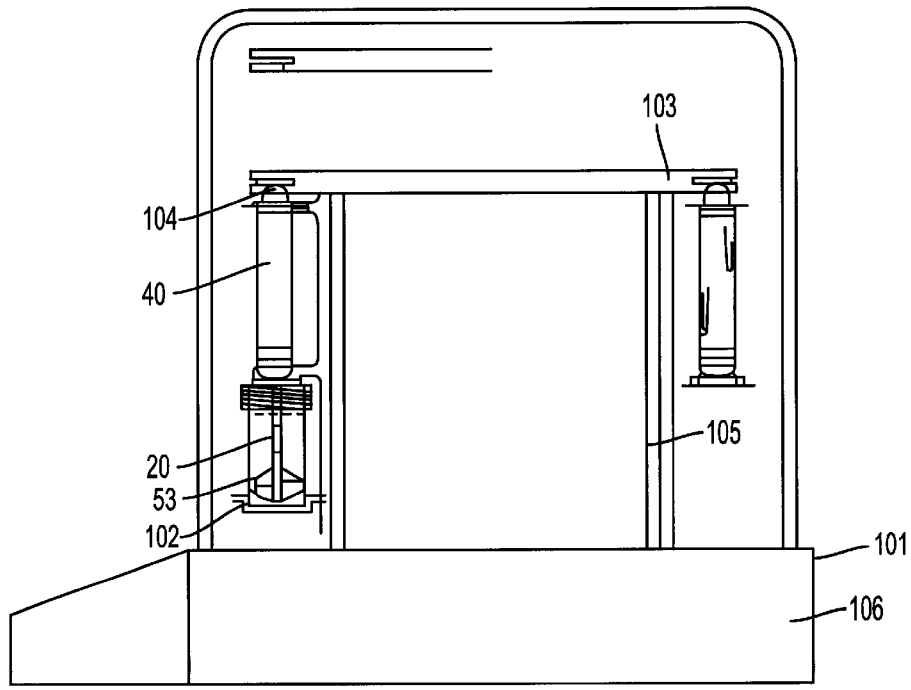
FIG. 19 is a side view of the mixing apparatus shown in FIG. 16.
Figure 20:
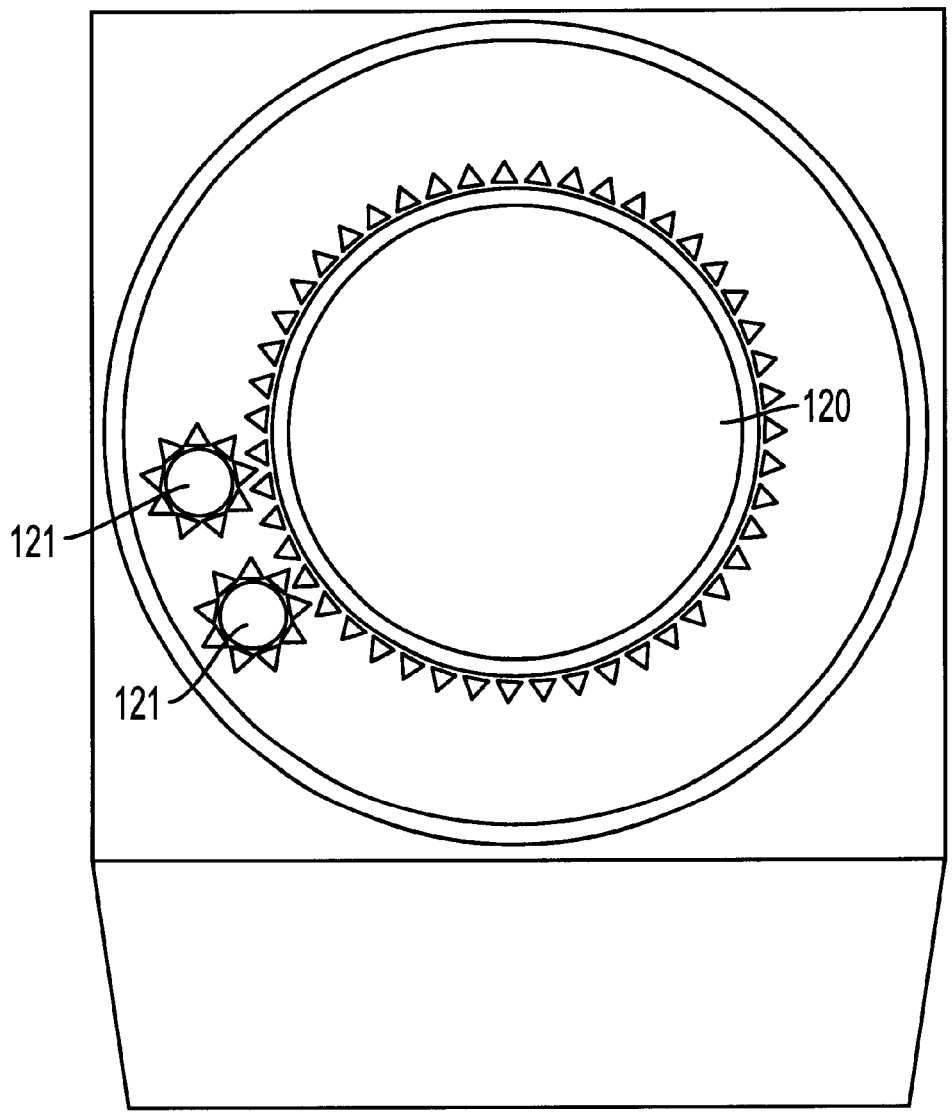
FIG. 20 is a bottom view of the mixing apparatus shown in FIG. 16 showing an exemplary drive mechanism.

FIGS. 13–15 show an apparatus for a semi-automated method according to a first preferred embodiment of the invention. In particular, FIGS. 13–15 show a most preferred embodiment comprising a support sleeve A for positioning and rotating the container and the inner cap 72. In the most preferred embodiment of the invention, the outer cap 71 is engaged by one or more resilient bands B that in a loosened or first position (FIG. 14) do not engage outer cap 71, and in a tightened or second position (FIG. 15) engage and hold the outer cap 71 while the inner cap 72 and container 20 are rotating. In an alternative embodiment, belt B may be a drive belt that rotates the outer cap 71, tube 50 and agitator 58, as a unit, with respect to container 20 and inner cap 72.

In accordance with a second preferred embodiment of the invention, the specimen collection and processing assembly 10 may be adapted for use with a processing apparatus shown generally as 100 in FIG. 12. Processing apparatus 100 includes a lower platform 101 having at least one, and preferably a plurality of, sockets 102 adapted to receive a bottom portion of specimen container 20. Specimen container 20 may fit snugly in socket 102, or socket 102 may include any of a variety of resilient members that position and hold the specimen container in place. An exemplary resilient member includes an O-ring or a rubber gasket.

Processing apparatus 100 also includes an upper platform 103 adapted to receive a top portion of pump 40, preferably a top portion of plunger 104. In a most preferred embodiment of the invention, upper platform 103 includes a recess, slot, notch, or opening adapted to receive the top portion of plunger 104.

Upper platform 103 is supported by moveable base 105, typically a cylinder or the like, that can be raised and lowered in relation to platform 101. Movement of upper platform 103 raises or lowers plunger 104 in relation to pump 40.

Lower platform 101 rests on or forms a portion of housing 106. Housing 106 encloses a centrally located drive or sun gear 120. Drive gear 120 is adapted to engage a plurality of planet gears 121 adapted to communicate with or corresponding to socket 102 or container 20. In a preferred embodiment of the invention, rotational movement of the sun gear turns each of the planet gears, which in turn rotate container 20 in relation to fin 53. Alternatively, planet gear 121 may include an element that engages and rotates fin 58.

In operation, a technician places or collects a liquid sample in container 20 and closes the container with a cover 31/pump 40 assembly. A bottom portion of container 20 is then positioned in socket 102 and a top portion of plunger 104 is positioned in a slot in upper platform 103. The technician may then activate a motor or the like that rotates sun gear 120, which in turn rotates planet gears 121, which in turn rotate container 20 around an axis. When mixing is complete, upper platform 103 is raised, drawing plunger 104 out of the pump body. Movement of the plunger draws sample in the container 20 through the particulate matter separation housing and through the porous arrangement and into the chamber in pump 40. Each of these steps may be repeated as often as desirable.

Kit

The present invention is also directed to a particulate matter collection and testing kit containing the collection apparatus 10 as an integral unit. The kit may include at least one specimen container 20, at least one particulate matter separation chamber 30, at least one pump 40, and at least one porous filter arrangement 35. A kit according to the invention may also include replacement filters, replacement disposables, and/or other components or solutions typically used during particulate matter testing or examination procedures, e.g., cytological examinations.

Method

The present invention also includes a method for removing particulate matter from a fluid, and for transferring particulate matter, such as cells, to a microscope slide. In contrast to currently available methods, the use of membrane filtration provides a method of depositing cells evenly over a microscope slide with minimal overlap. This allows for clear observation and optimal diagnostic accuracy.

A method includes collecting a fluid sample containing particulate matter in a collection container 20. The container 20 is then capped with an assembly that includes one or more of the following: cap 31, particulate matter separation chamber 30, and pump 40. Pump 40 is then activated to pull fluid from container 20 through particulate matter separation chamber 30 into pump 40, e.g., by withdrawing the piston in a syringe.

Figure 3:
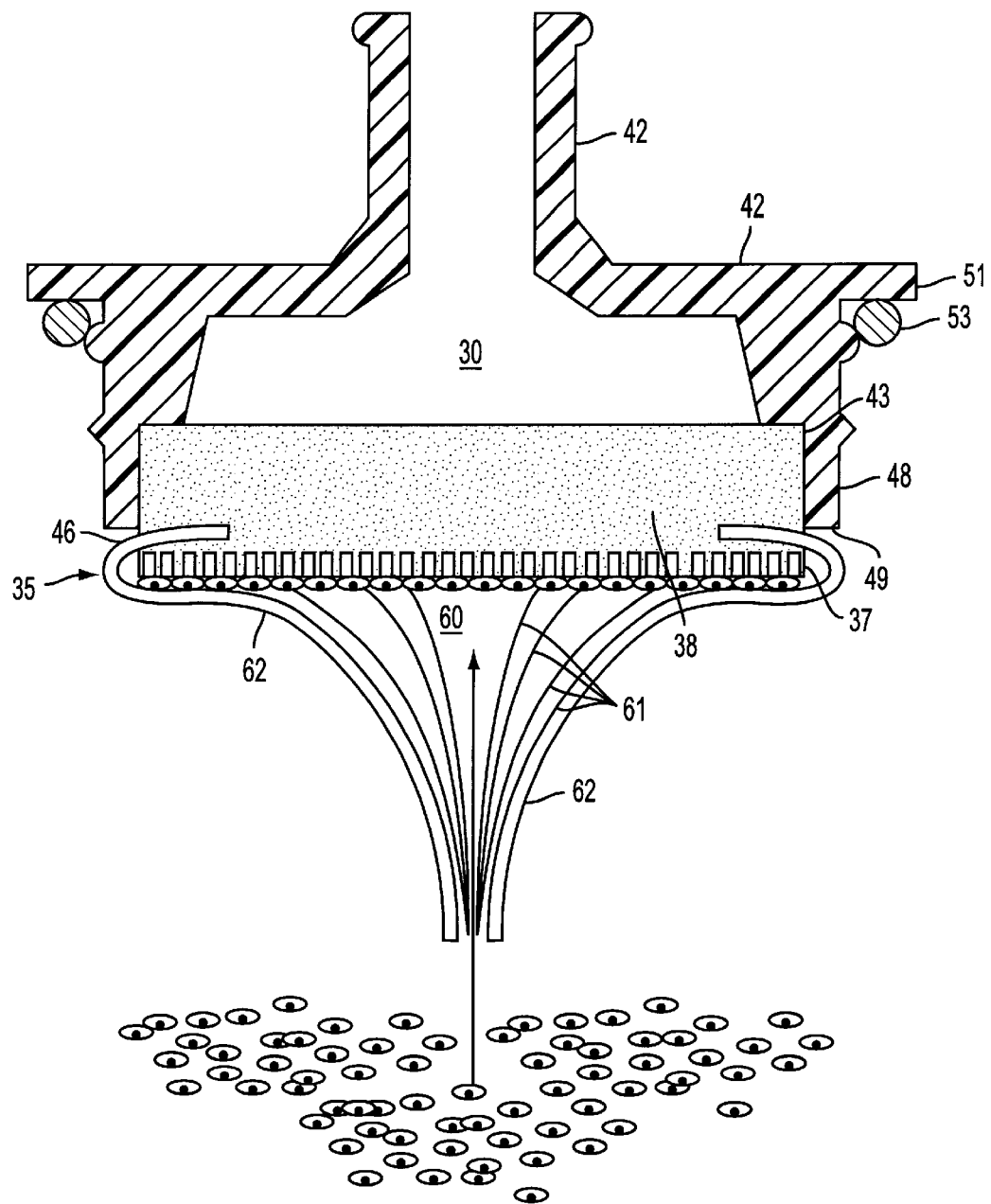
FIG. 3 is a cross section view of the fluid flow paths through the particulate matter separation chamber.

When the fluid is pulled from the container 20 to the pump 40, fluid will flow through porous filter arrangement 35 as shown in FIG. 3, so that a monolayer of particulate matter is formed on collection site 37. Once the monolayer of cells is formed, fluid flow is reduced in the center of porous filter arrangement 35 and increases towards the edges of the porous filter arrangement 35. This may be due to the blockage of fluid flow by the collected cells as they form the monolayer on the surface of the porous filter arrangement 35. When the monolayer has mostly covered the surface 45 of the porous arrangement, the flow of fluid bypasses the first porous medium 37 and passes through the extended side area of the second porous medium 38. Thus, the area of the second porous medium 38 extending beyond an end wall or skirt of the top portion acts as a vent (with low resistance to flow) that prevents cells piling up or collecting in more than a monolayer. Fluid may be passed back and forth through the porous arrangement as many times as desirable.

Pump 40 may then be disconnected from base 31, and thereby exposing porous filter arrangement 35. Once porous filter arrangement 35 is removed from lower portion 32, easy access is gained to first porous medium 37. Alternatively, disengaging top portion 41 of pump 40 from lower portion 32 may also remove porous arrangement 35 from well 32.

The first porous medium 37 may then be pressed against a microscope slide to allowing particulate matter collected on the collection site to be transferred, as they were collected, onto the slide. This allows a cytological examination to be performed on the cells by the practitioner without the interference of the pores in the membrane or delay due to processing requirements.

Since cellular detail is dependent on fixation, it is preferred that cells be fixed immediately after being deposited on the slide. Too long a delay between preparation and fixation may expose the cells to drying, which may be detrimental to the cellular structure. Moreover, air-drying artifacts can adversely affect the subsequent staining results. An exception is when the cells are stained with Wright-Giemsa, where air-drying is used as the fixation step.

In an another embodiment of the present invention, the monolayer of cells may be fixed directly on the collection site. This may be carried out by first depositing a monolayer of cells on the collection site of the cytology collection apparatus as described above and subsequently passing a solution containing a fixative, such as alcohol or acetone, through the cytology collection apparatus.

Alternative Configurations

The matter collection apparatus or module described above may be used in combination with other suitable filtration or treatment devices. Exemplary devices include other debris and/or assay devices or modules that may be attached to housing 10. Typically, these additional modules will include a housing having an inlet and an outlet, and will include a filtration, assay, or detection element positioned across the fluid flow path in the housing. For example, the apparatus may comprise a housing including inlet and outlet ports defining a flow path between the inlet and the outlet; a filter positioned across the flow path; and a freely movable chromatography/assay element, such as substrate beads, positioned on the outlet side of the filter. The chromatography/assay element can freely mix with the matter in the fluid, capture the matter, and can then be assayed for the presence of the matter. Suitable devices include those disclosed in U.S. Pat. Nos. 4,953,561; 5,224,489; 5,016,644; 5,139,031; 5,301,685; 5,042,502 and 5,137,031, which are incorporated by reference.

Included within the scope of the present invention is producing a single slide from a patient sample, producing multiple slides from a single patient sample, or producing multiple slides from multiple patient samples. It is intended that a patient sample may be processed in a single shot, batch, or continuous manner. Additional slides for other stain applications can be easily prepared. Human papilloma virus testing, for example, by newer methods such as immunocytochemistry or in-situ hybridization can be performed on the additional slides. As oncogene products or other immunocytochemical tests are developed, more slides may be necessary. The different fixations that these tests may need can easily be incorporated into the procedure since the preparation does not require the slides to be fixed in only one way.

The most widely used stain for visualization of cellular changes in cytology is the Papanicolaou staining procedure. This stain, which is used for both gynecologic and non-gynecologic applications, is basically composed of blue nuclear and orange, red and green cytoplasmic counterstains. The nuclear stain demonstrates the chromatic patterns associated with normal and abnormal cells, while the cytoplasmic stains help to indicate cell origin. he success of this procedure can be attributed to the ability to observe a number of factors, including definition of nuclear detail and cell differentiation. This staining procedure also results in a multicolor preparation that is very pleasing to the eye, possibly reducing eye strain. This same slide preparation procedure can be used for virtually all forms of cytology.

Furthermore, the use of completely contained disposable components addresses biohazard concerns. Ultimately, the enhanced presentation of cells, yielding improved cytologic interpretation, may expand the role of cytology by providing more consistent and reliable patient diagnosis.

Also, captured microorganisms can be cultured in culture medium. After a monolayer of cells has been collected in the cytology collection apparatus, fluid may be used to back-flush the collection site, thereby transferring any collected microorganisms from the collection site.

In bacteria testing, the first porous medium can be used for culturing with a Qualture device (not shown) to determine the presence of specific bacteria colonies. The Qualture device is a plastic capsule containing a filter membrane and four nutrient pads of dehydrated, selective media.

The Qualture technique is more sensitive than the agar plate method and more rapid in determining a presumptive diagnosis. The device screens, isolates and presumptively diagnoses bacterial isolates in one step most often in 4–6 hours. Tests have demonstrated that recovery from fifty milliliters of fluid is excellent and sensitive.

Although the present invention has been described in terms of a particular preferred embodiments, it is not limited to those embodiments. Alternative embodiments, examples, and modifications that would still be encompassed by the invention may be made by those skilled in the art, particularly in light of the foregoing teachings.

What is claimed is:

1. An apparatus for simultaneously processing a plural number of samples, each of the samples including a fluid containing particulate matter, the apparatus comprising:

a plural number of processing assemblies corresponding to said plural number of samples, each of said processing assemblies comprising:

a container adapted to contain one of the samples;

an agitator supported so that it extends into said container, contacts the sample therein and can rotate relative to said container to disperse particulate matter in the fluid of that sample;

a filter assembly including a filter adapted to collect particulate matter from the sample in said container; and a pump in communication with said filter assembly and adapted to move the particulate matter-containing fluid of the sample in said container through said filter;

a container engagement comprising a plural number of container receivers corresponding to said plural number of samples, each of said container receivers engaging one of said containers;

a pump engagement comprising a plural number of pump receivers corresponding to said plural number of container receivers, each of said pump receivers associated with a respective container receiver and engaging the pump associated with the container engaged by its respective container receiver; and a rotary driver for effecting relative rotation of said agitators and their respective containers simultaneously to mix the samples in said containers.

2. The apparatus according to claim 1, wherein said pump engagement reciprocates relative to said container engagement to actuate said pumps simultaneously and move the fluid samples through their respective filters.

3. The apparatus according to claim 2, wherein each of said processing assemblies comprises a cover assembly for said container, said cover assembly engaging said pump and having a portion that is rotatable relative to said container.

4. The apparatus according to claim 3, wherein said filter assembly is disposed within said cover assembly.

5. The apparatus according to claim 4, comprising a cover engagement that engages the rotatable portion of each of said covers, each of said container receivers being rotatable relative to said cover engagement to effect relative rotation of each agitator and its respective container.

6. The apparatus according to claim 5, wherein said cover engagement comprises a number of resilient bands corresponding to the number of containers, each of said resilient bands frictionally engaging the rotatable portion of a respective one of said cover assemblies.

7. The apparatus according to claim 6, wherein each of said resilient bands is movable between a position frictionally engaging its respective rotatable cover portion and a position out of engagement with its respective rotatable cover portion.

8. The apparatus according to claim 6, wherein each of said container receivers rotates relative to said container engagement and its respective resilient band.

9. The apparatus according to claim 2, wherein each of said agitators is rotatably fixed relative to its respective pump, and each of said container receivers rotates relative to its respective pump receiver to effect relative rotation of each agitator and its respective container.

10. The apparatus according to claim 9, wherein each of said container receivers rotates relative to said container engagement.

11. The apparatus according to claim 10, wherein all of said container receivers are driven by a common drive.

12. The apparatus according to claim 1, wherein each of said agitators is rotatably fixed relative to its respective pump, and each of said container receivers is rotatable relative to its respective pump receiver to effect relative rotation of each agitator and its respective container.

13. The apparatus according to claim 12, wherein each of said processing assemblies comprises a cover assembly for said container, said cover assembly engaging said pump and having a portion that is rotatable relative to said container.

14. The apparatus according to claim 13, comprising a cover engagement that engages the rotatable portion of each of said covers, each of said container receivers being rotatable relative to said cover engagement to effect relative rotation of each agitator and its respective container.

15. The apparatus according to claim 14, wherein said cover engagement comprises a number of resilient bands corresponding to the number of containers, each of said resilient bands frictionally engaging the rotatable portion of a respective one of said cover assemblies.

16. The apparatus according to claim 15, wherein each of said resilient bands is movable between a position frictionally engaging its respective rotatable cover portion and a position out of engagement with its respective rotatable cover portion.

17. The apparatus according to claim 15, wherein each of said container receivers rotates relative to said container engagement and its respective resilient band.

18. The apparatus according to claim 12, wherein each of said container receivers rotates relative to said container engagement.

19. The apparatus according to claim 18, wherein all of said container receivers are driven by a common drive.

20. The apparatus according to claim 19, wherein said common drive comprises a planetary gear associated with each of said container receivers and a sun gear driving each of said planetary gears.

* * * * *